(12) United States Patent
Yaffe et al.

(10) Patent No.: US 12,226,141 B2
(45) Date of Patent: Feb. 18, 2025

(54) THIN FILM MAPPING CATHETER

(71) Applicant: Verily Life Sciences LLC, South San Francisco, CA (US)

(72) Inventors: Benjamin K. Yaffe, South San Francisco, CA (US); Bo Lu, South San Francisco, CA (US); Annapurna Karicherla, South San Francisco, CA (US); Ken Rys, South San Francisco, CA (US); Ohseung Kwon, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 586 days.

(21) Appl. No.: 17/622,577

(22) PCT Filed: Jun. 5, 2020

(86) PCT No.: PCT/US2020/036355
§ 371 (c)(1),
(2) Date: Dec. 23, 2021

(87) PCT Pub. No.: WO2020/263534
PCT Pub. Date: Dec. 30, 2020

(65) Prior Publication Data
US 2022/0370113 A1 Nov. 24, 2022

Related U.S. Application Data

(60) Provisional application No. 62/867,535, filed on Jun. 27, 2019.

(51) Int. Cl.
*A61B 18/02* (2006.01)
*A61B 5/00* (2006.01)
*A61B 18/00* (2006.01)

(52) U.S. Cl.
CPC ............ *A61B 18/02* (2013.01); *A61B 5/6853* (2013.01); *A61B 2018/00077* (2013.01); *A61B 2018/00839* (2013.01); *A61B 2018/0212* (2013.01)

(58) Field of Classification Search
CPC ..... A61B 18/02; A61B 5/6853; A61B 5/6858; A61B 2018/00077; A61B 2018/00839; A61B 2018/0212
See application file for complete search history.

(56) References Cited

U.S. PATENT DOCUMENTS

| | | | |
|---|---|---|---|
| 2013/0172883 A1* | 7/2013 | Lopes | A61B 5/287 606/41 |
| 2014/0262462 A1 | 9/2014 | Shah et al. | |

(Continued)

FOREIGN PATENT DOCUMENTS

| | | | | |
|---|---|---|---|---|
| WO | WO-2019141284 A1 * | 7/2019 | ............. | A61B 18/02 |
| WO | WO-2019108664 A3 * | 8/2019 | ............. | A61B 18/14 |

OTHER PUBLICATIONS

Kang et al., "A review: flexible, stretchable multifunctional sensors and actuators or heart arrhythmia therapy", Micro and Nano Systems Letters, 5:22, 2017, 8 pages.

(Continued)

*Primary Examiner* — Ankit D Tejani
*Assistant Examiner* — Joshua Brendon Solomon
(74) *Attorney, Agent, or Firm* — Kilpatrick Townsend & Stockton LLP

(57) ABSTRACT

The present disclosure relates to mapping catheters, and in particular to mapping catheters having thin film electrodes used in sensing electrical activity within a patient. Particularly, aspects of the present disclosure are directed to a medical device having a hollow core, a balloon disposed over at least a portion of the hollow core, and a flexible framework having one or more thin film elements formed on (Continued)

at least a portion of the balloon. The one or more thin film elements comprise a plurality of mapping electrodes.

17 Claims, 18 Drawing Sheets

(56) References Cited

U.S. PATENT DOCUMENTS

| | | | |
|---|---|---|---|
| 2015/0157391 A1* | 6/2015 | Ben-Ezra | A61N 7/00 |
| | | | 606/41 |
| 2015/0250982 A1* | 9/2015 | Osypka | A61B 18/02 |
| | | | 606/108 |
| 2017/0027640 A1 | 2/2017 | Kunis et al. | |
| 2017/0189106 A1* | 7/2017 | Schuler | A61B 5/287 |
| 2019/0282116 A1* | 9/2019 | Olson | A61B 5/287 |
| 2020/0359967 A1* | 11/2020 | Feng | A61B 5/6856 |
| 2020/0375657 A1* | 12/2020 | Olson | A61M 25/0026 |

OTHER PUBLICATIONS

Kim et al., "Flexible and Stretchable Electronics for Biointegrated Devices", Annual Review of Biomedical Engineering, vol. 14, 2012, pp. 113-128.

Lee et al., "Catheter-Based Systems With Integrated Stretchable Sensors and Conductors in Cardiac Electrophysiology", Proceedings of the IEEE, vol. 103, No. 4, Apr. 2015, pp. 682-689.

Mantziari et al., "Utility of a Novel Rapid High-Resolution Mapping System in the Catheter Ablation of Arrhythmias: An Initial Human Experience of Mapping the Atria and the Left Ventricle", JACC: Clinical Electrophysiology, vol. 1, No. 5, Oct. 2015, pp. 411-420.

Application No. PCT/US2020/036355, International Search Report and Written Opinion, Mailed On Sep. 10, 2020, 8 pages.

* cited by examiner

Cross-sectional view of
non-expandable regions mounted on tubing

Cross-sectional view of
expandable regions glued to blow molded balloon

THIN FILM MAPPING CATHETER

CROSS-REFERENCE TO RELATED APPLICATION

The present application is a national phase filing of International Patent Application No. PCT/US2020/036355, filed Jun. 5, 2020, which claims priority and benefit from U.S. Provisional Application No. 62/867,535, filed Jun. 27, 2019, the entire contents of which are incorporated herein by reference for all purposes.

FIELD

The present disclosure relates to mapping catheters, and in particular to mapping catheters having thin film electrodes used in sensing electrical activity within a patient.

BACKGROUND

Electrical mapping of a biological system is a procedure that may be used to detect normal or abnormal electrical activity within the biological system. For example, electrical mapping of the heart is a procedure that is used to diagnose the origins of arrhythmias. An arrhythmia may be diagnosed when a heartbeat is too fast, too slow or irregular (uneven). Arrhythmias may be caused by problems with the heart's electrical system. The electrical signals may fire too fast or too slowly, or in an uneven irregular) way. Abnormal electrical signals can originate in different areas of the heart (such as the atria or ventricles) causing arrhythmias, begin an electrical mapping procedure, a mapping catheter may be inserted through a small incision in the patient and guided through the blood vessels until it is inside the biological system such as the heart. The mapping catheter can be used to sense electrical activity and map the activity on a three-dimensional model of the biological system.

A healthcare provider can use the three-dimensional model to perform procedures such as pulmonary vein isolation via radiofrequency ablation or cryoablation. Pulmonary vein isolation is a procedure used to stop abnormal electrical signals in the heart that cause heart rhythm problems. Radiofrequency ablation employs an electrical current produced by a radio wave to heat up a small area of nerve tissue to stop it from sending electrical signals. In contrast, cryoablation employs liquid nitrous oxide that is delivered under pressure within a balloon to freeze the surrounding nerve tissue. Cryoablation is capable of achieving, circumferential pulmonary vein isolation more efficiently, compared to traditional point-by-point radiofrequency ablation.

In pulmonary vein isolation, conventional medical systems use a double-catheter technique for carrying (i) the mapping electrodes, and (ii) the medical therapy device (e.g., electrodes for radiofrequency ablation or the balloon for cryoablation). A mapping catheter is used to map and provide real-time pulmonary vein potentials, usually before and after medical therapy to confirm the effect of pulmonary vein isolation. A medical therapy catheter is used to provide the therapy such as radiofrequency ablation or cryoablation in accordance with the three-dimensional model generated by the mapping catheter. However, the telescoped architecture of a double-catheter technique is problematic as the mapping electrodes are large, resulting in a balloon or electrode device with a large core lumen. This limits the flexibility and accuracy in placement of the therapy device and limits the healthcare provider in treatment options. Therefore, there is a need to reduce the overall size of the mapping catheter and improve upon the double-catheter technique.

BRIEF SUMMARY

In various embodiments, a medical device is provided comprising: a hollow core balloon disposed over at least a portion of the hollow core; and a flexible framework comprising one or more thin film elements formed on at least a portion of the balloon, where the one or more thin film elements comprise a plurality of mapping electrodes.

In some embodiments, the medical device further comprises: an end cap; a sheath, where the hollow core extends between the end cap and the sheath; and a travel limiter disposed between the one or more thin film elements and the hollow core.

In some embodiments, the one or more thin film elements are made of one or more layers of dielectric material.

In some embodiments, the dielectric material is a polymer of imide monomers, a liquid crystal polymer (LCP), parylene, polyether ether ketone (PEEK), or any combination thereof.

In some embodiments, the plurality of mapping electrodes are comprised of one or more layers of conductive material, and the conductive material is platinum (Pt), platinum/iridium (Pt/Ir), titanium (Ti), gold/titanium (Au/Ti), any alloy thereof, or any combination thereof.

In some embodiments, the medical device further comprises a guide wire disposed in the sheath and extending from an opening in the end cap.

In some embodiments, the one or more thin film elements further comprise a plurality of conductive tracings in electrical communication with the plurality of mapping electrodes.

In some embodiments, the medical device further comprises a proximal hub positioned on or within the sheath, where: the sheath comprises a channel; and the one or more thin film elements extend through the channel of the sheath and connect with the proximal hub.

In some embodiments, the medical device further comprises a pull cable disposed within the sheath and attached to the end cap or the hollow core for retracting the hollow core and anchoring the travel limiter to a distal end of the sheath.

In some embodiments, where: the one or more thin film elements are a plurality of thin film elements; each thin film element of the plurality of thin film elements extends longitudinally from a distal end of the sheath to the end cap; and each thin film element of the plurality of thin film elements is attached to the end cap.

In some embodiments, where: the one or more thin film elements are a single thin film element; the single thin film element extends from a distal end of the sheath to the end cap in a helix around the balloon; and the single thin film element is attached to the end cap.

In some embodiments, the balloon is a cryoballoon.

In various embodiments, a medical device is provided comprising: a sheath; an end cap; a hollow core extending from the sheath to the end cap; a plurality of thin film elements disposed around the hollow core, where the plurality of thin film elements comprise a plurality of mapping electrodes; and a travel limiter disposed between the plurality of thin film elements and the hollow core.

In some embodiments, the plurality of thin film elements are made of one or more layers of dielectric material.

In some embodiments, the dielectric material is a polymer of imide monomers, a liquid crystal polymer (LCP), parylene, polyether ether ketone (PEEK), or any combination thereof.

In some embodiments, the plurality of mapping electrodes are comprised of one or more layers of conductive material, and the conductive material is platinum (Pt), platinum/iridium (Pt/Ir), titanium (Ti), gold/titanium (Au/Ti), any alloy thereof, or an combination thereof.

In some embodiments, the medical device further comprises a guide wire disposed in the sheath and extending from an opening in the end cap.

In some embodiments, the plurality of thin film elements further comprise a plurality of conductive tracings in electrical communication with the plurality of mapping electrodes.

In some embodiments, the medical device further comprises a proximal hub positioned on or within the sheath, where: the sheath comprises a channel; and the plurality of thin film elements extend through the channel of the sheath and connect with the proximal hub.

In some embodiments, the medical device further comprises a pull cable disposed within the sheath and attached to the end cap or hollow core for retracting the hollow core and anchoring the travel limiter to a distal end of the sheath.

In some embodiments, where: each thin film element of the plurality of thin film elements extends from a distal end of the sheath to the end cap in a straight line parallel to a central axis of the hollow core; and each thin film element of the plurality of thin film elements is attached to the end cap.

In some embodiments, where: each thin film element of the plurality of thin film elements extends from a distal end of the sheath to the end cap in a helix around the hollow core; and each thin film element of the plurality of thin film elements is attached to the end cap.

In various embodiments, a medical system is provided comprising: a mapping catheter comprising: a sheath comprising a proximal end, a distal end, a channel, and a hub disposed at the proximal end; an end cap; a hollow core extending from the distal end of the sheath to the end cap; a flexible framework comprising a plurality of longitudinal extending arms disposed around the hollow core, where the plurality of longitudinal extending arms comprise a plurality of mapping electrodes, distal ends of the plurality of longitudinal extending arms are attached to the end cap, the plurality of longitudinal extending arms extend through the channel of the sheath, and proximal ends of the plurality of longitudinal extending arms are attached to the hub; and a travel limiter attached to the end cap and disposed between the plurality of longitudinal extending arms and the hollow core. The medical system further comprises a treatment catheter disposed over at least a portion of the mapping catheter.

In some embodiments, the treatment catheter is a cryoballoon catheter comprising a cryoballoon disposed over a hollow body, and where the hollow body is disposed over the sheath of the mapping catheter.

In some embodiments, the plurality of longitudinal extending arms further comprise a plurality of conductive tracings in electrical communication with the plurality of mapping electrodes and the hub.

In some embodiments, the medical system further comprises a pull cable disposed within the hollow core and attached to the end cap for retracting the hollow core and anchoring the travel limiter to the distal end of the sheath.

In some embodiments, each arm of the plurality of longitudinal extending, arms extends from the distal end of the mapping catheter to the end cap in a straight line parallel to a central axis of the hollow core.

In some embodiments, each arm of the plurality of longitudinal extending arms extends from the distal end of the sheath to the end cap in a helix around the hollow core.

In various embodiments, a method is provided for deploying a medical device. The method comprises inserting the medical device into a cavity of a body, where the medical device includes: a sheath; an end cap; a hollow core extending from the sheath to the end cap; a plurality of thin film elements disposed in a first configuration around the hollow core, where the plurality of thin film elements comprise a plurality of mapping electrodes; and a travel limiter disposed between the plurality of thin film elements and the hollow core. The method further comprises providing tension on a pull cable to retract the end cap towards a distal end of the sheath and retract the hollow core within the sheath; anchoring the travel limiter to the distal end of the sheath; and expanding the plurality of thin film elements to a second configuration.

In some embodiments, in the first configuration: each thin film element of the plurality of thin film elements extends from the distal end of the sheath to the end cap in a straight line parallel to a central axis of the hollow core; and each thin film element of the plurality of thin film elements is attached to the end cap.

In some embodiments, in the second configuration, each of the thin fid elements take on a bell shaped curve.

In some embodiments, the first configuration: each thin film element of the plurality of thin film elements extends from the distal end of the sheath to the end cap in a helix around the hollow core; and each thin film element of the plurality of thin film elements is attached to the end cap.

In some embodiments, in the second configuration, each of the thin film elements take on a coil shape comprising end portions and a center, and where the end portions have a smaller radius than a radius of the central portion.

In various embodiments, a medical device is provided comprising: a sheath; a balloon disposed over at least a portion of the sheath; and a flexible framework comprising an expandable region and a non-expandable region, where: the expandable region comprises a plurality of longitudinal extending aims, each arm of the plurality of longitudinal extending arms comprises one or more layers of dielectric material, one or more conductive traces, and one or more electrodes electrically connected to the one or more conductive traces, the expandable region is formed on an inflatable portion of the balloon, the non-expandable region comprises one or more layers of dielectric material, the one or more conductive traces, and one or more contacts electrically connected to the one or more conductive traces, and the non-expandable region is formed on a non-inflatable portion of the balloon or the sheath; and a cable comprising a plurality of wires electrically connected to the one or more contacts.

In some embodiments, the cable is integrated into the sheath or runs through a lumen or channel of the sheath.

In some embodiments, the one or more dielectric layers of the expandable region comprises a polymer of imide monomers, a liquid crystal polymer (LCP), parylene, polyether ether ketone (PEEK), or any combination thereof.

In some embodiments, the one or more dielectric layers of, the non-expandable region comprises a polymer of imide monomers, a liquid crystal polymer (LEP), a thermoplastic polyurethane (TPU), or any combination thereof.

BRIEF DESCRIPTION OF THE DRAWINGS

The present invention will be better understood in view of the following, non-limiting figures, in which.

DETAILED DESCRIPTION

I. Introduction

Figure 1A:
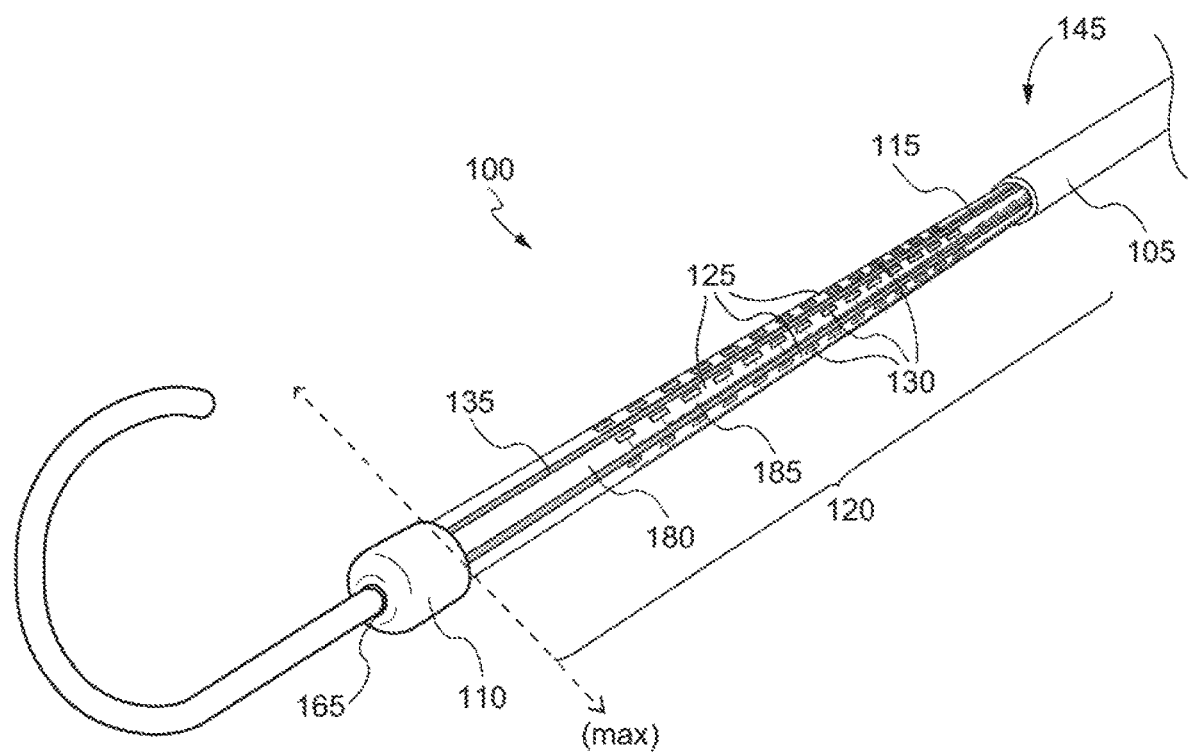
FIG. 1A shows a perspective view of a medical device in accordance with various embodiments.

The following disclosure describes medical devices or mapping catheters having thin film electrodes used in sensing electrical activity within a patient. In various embodiments, an integrated catheter technique: is provided capable of performing mapping and medical therapy in a sequential or simultaneous manner using a single catheter comprising mapping electrodes disposed on at least a portion of a medical therapy balloon (e.g., an ablation or cryoablation balloon). In some embodiments, a medical device includes a sheath, a balloon disposed over at least a portion of the sheath, and a flexible framework comprising one or more thin film elements formed on at least a portion of the balloon. The one or more thin film elements comprise a plurality of mapping electrodes configured to generate a three-dimensional model of a biological system. In some embodiments, each of the one or more thin film elements comprises: (i) an expandable region formed on the balloon, the expandable region comprising a polymer, layer, a wiring layer, and the plurality of mapping electrodes electrically connected to the wiring layer, and (ii) a non-expandable region formed on the sheath, the non-expandable, region comprising a second polymer layer and the wiring layer. The first polymer layer may be formed in the shape of a structure (e.g., a serpentine) that allows for the flexible framework to be expanded, contracted, opened, or closed in order to position the flexible framework on balloon and to allow for the balloon to be inflated without the wiring layer cracking or breaking apart.

In alternative embodiments, a double-catheter technique is provided capable of performing mapping and medical therapy in a sequential or simultaneous manner using a medical therapy catheter (e.g., an ablation or cryoablation catheter) disposed over at least a portion of a mapping catheter. In some embodiments, the mapping catheter includes a flexible framework comprising one or more thin an elements extending from a distal end of a hollow body (e.g., a sheath) and disposed around a hollow core. The one or more thin film elements comprise a plurality of mapping electrodes configured to generate a three-dimensional model of a biological system. In some embodiments, the medical device further comprises a travel limiter disposed between the one or more thin film elements and the hollow core. As used herein, the term "proximal" or "proximal end" refers to a first end of the element or component, while the term "distal" or "distal end" refers to a second end opposing the first end. For example, the proximal end may be an end of the element or component, which is closest to the user, and the distal end may be an end of the element or component, which is furthest from the user. In some embodiments, the medical therapy catheter is a cryoballoon catheter comprising a cryoballoon disposed over a hollow body, and the hollow body is disposed over the sheath of the mapping catheter.

The flexible framework may be fabricated using microfabrication techniques. As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 μm). Thin films may be deposited by applying a very thin film of material (e.g., between a few nanometers to about 100 μm) onto a substrate surface to be coated, or onto a previously deposited layer of thin film. In various embodiments, thin film elements are provided comprising a base polymer body (e.g., a supporting structure), at least one electrode formed on the base polymer body, and at least one conductive trace formed on the base polymer body and in electrical communication or contact with the at least one electrode. In some embodiments, the thin film elements have a high density neural interface. As used herein, the term "high density neural interface(s)" refers to a neural interface that comprises at least sixteen electrodes (i.e., recording, sensing, stimulating, other types of electrodes, or combinations thereof).

As described herein, a double-catheter technique typically comprises (i) the mapping catheter, and (ii) the medical therapy catheter. The mapping catheter is used before medical therapy to generate a three-dimensional model of a biological system, and after medical therapy to confirm the effect of the medical therapy. The medical therapy catheter is used to provide the therapy such as radiofrequency ablation or cryoablation in accordance with the three-dimensional model generated by the mapping catheter. However, the telescoped architecture of the conventional double-catheter technique is problematic as the mapping electrodes are large, resulting in a balloon or electrode device with a large core lumen. This limits the flexibility and accuracy in placement and limits the healthcare provider in treatment options. Moreover, the conventional double-catheter technique typically requires deployment of the mapping catheter to generate the three-dimensional model, subsequent deployment of the medical therapy catheter and inflation of the balloon to provide the therapy in accordance with the three-dimensional model, and then subsequent redeployment of the mapping catheter to determine whether the therapy was successful. However, the serial processing of the conventional double-catheter technique is problematic as the deployment and redeployment of each catheter adds complexity and time into the surgical process. This further limits the healthcare provider in treatment options.

To address these limitations and problems, the electrodes of various embodiments disclosed herein are formed on a flexible framework capable of taking a first configuration during insertion into the patient and then deployed as a second configuration during mapping. The electrodes and optional other sensors (e.g. temperature, tactile) are formed on thin films of polymer or similar material. The use of thin films not only reduces the form factor of all, catheters in the system (e.g., the mapping catheter and the medical therapy catheter) by reducing the size of the mapping catheter, but also enables integration of more mapping electrodes along the flexible framework due to their, much smaller size and the integration of traces into the polymer or other thin film material. Additionally, the reduction in form factor and increase in the number of electrodes capable of being formed on the flexible framework allows for the potential addition of other types of sensors to achieve a more versatile system. Moreover, it was surprisingly discovered that medical therapy such as cryoablation does not harm or break thin films of polymer or similar material, and thus it has been found possible to integrate the thin films directly on the medical therapy balloons for sequential or simultaneous mapping and medical therapy.

One illustrative embodiment of the present disclosure is directed to a sheath; a balloon disposed over at least a portion of the sheath; and a flexible framework comprising one or more thin film elements formed on at least a portion of the balloon. The one or more thin film elements comprise a plurality of mapping electrodes. In some embodiments, the one or more thin film elements are a plurality of thin film elements; each thin film element of the plurality of thin film elements extends from a distal end of the sheath to the end cap in a straight line parallel to a central axis of the hollow core; and each thin film element of the plurality of thin film elements is attached to the end cap. In other embodiments, the one or more thin film elements are a single thin film element; the single thin film element extends from a distal end of the sheath to the end cap in a helix around the balloon; and the single thin film element is attached to the end cap.

In other embodiments, a medical device is provided comprising a sheath; an end cap; a hollow core extending from the sheath to the end cap; a plurality of thin film elements disposed around the hollow core, the plurality of thin film elements comprise a plurality of mapping electrodes; and a travel limiter disposed between the plurality of thin film elements and the hollow core. In some embodiments, each thin film element of the plurality of thin film elements extends from a distal end of the sheath to the end cap in a straight line parallel to a central axis of the hollow core. In alternative embodiments, each thin film element of the plurality of thin film elements extends from a distal end of the sheath to the end cap in a helix around the hollow core.

In other embodiments, a medical system is provided comprising: a mapping catheter comprising: a sheath comprising a proximal end, a distal end, a channel, and a hub disposed at the proximal end; an end cap; a hollow core extending from the distal end of the sheath to the end cap; a flexible framework comprising a plurality of longitudinal extending arms disposed around the hollow core, where the plurality of longitudinal extending anus comprise a plurality of mapping electrodes, distal ends of the plurality of longitudinal extending arms are attached to the end cap, the plurality of longitudinal extending arms extend into the channel of the sheath, and proximal ends of the plurality of longitudinal extending arms are attached to the hub; and a travel limiter attached to the end cap and disposed between the plurality of thin film elements and the hollow core; and a treatment catheter disposed over at least a portion of the mapping catheter.

In other embodiments, a method is provided for deploying a medical device. The method comprises inserting the medical device into a cavity of a body, where the medical device includes a sheath; an end cap; a hollow core extending from the sheath to the end cap; a plurality of thin film elements disposed in a first configuration around the hollow core, the plurality of thin film elements comprise a plurality of mapping electrodes; and a travel limiter disposed between the plurality of thin film elements and the hollow core. The method further comprises providing tension on a pull cable to retract the end cap towards a distal end of the sheath and retract the hollow core within the sheath; anchoring the travel limiter to the distal end of the sheath; and expanding the plurality of thin film elements to a second configuration.

In other embodiments, a medical device is provided comprising a sheath; a balloon disposed over at least a portion of the sheath; and a flexible framework comprising an expandable region and a non-expandable region. The expandable region comprises a plurality of longitudinal extending anus, each arm of the plurality of longitudinal extending anus comprises one or more layers of dielectric material, one or more conductive traces, and one or more electrodes electrically connected to the one or more conductive traces, the expandable region is formed on an inflatable portion of the balloon, the non-expandable region comprises one or more layers of dielectric material, the one or more conductive traces, and one or more contacts electrically connected to the one or more conductive traces, and the non-expandable region is formed on a non-inflatable portion of the balloon or the sheath. The medical device further comprises a cable comprising a plurality of wires electrically connected to the one or more contacts.

Advantageously, these approaches provide a medical device or system, which has increased pitch of electrodes and conductive traces, a smaller footprint, and greater design flexibility. More specifically, these approaches enable mapping catheters with higher electrode density and more detailed sensing while a medical treatment device with a narrower lumen can achieve more complete ablation coverage with increased surface area. Additionally, these approaches allow for mapping and medical therapy to be performed sequentially or simultaneously. This solution is scalable to provide many electrodes (e.g., sixteen or more), and thus enabling detailed sensing and mapping to model the electrical activity of the site of a biological system. Furthermore even for applications where multiple electrodes are not required, various embodiments can be miniaturized to increase flexibility and accuracy in placement of the medical treatment device and provide greater treatment options for the healthcare provider. It should be understood that although ablation and pulmonary vein isolation are provided as examples of some embodiments, this solution is applicable to any mapping catheter designed to sense electrical activity of a site of a biological system.

II. Dual Catheter Devices and Systems

Figure 1B:
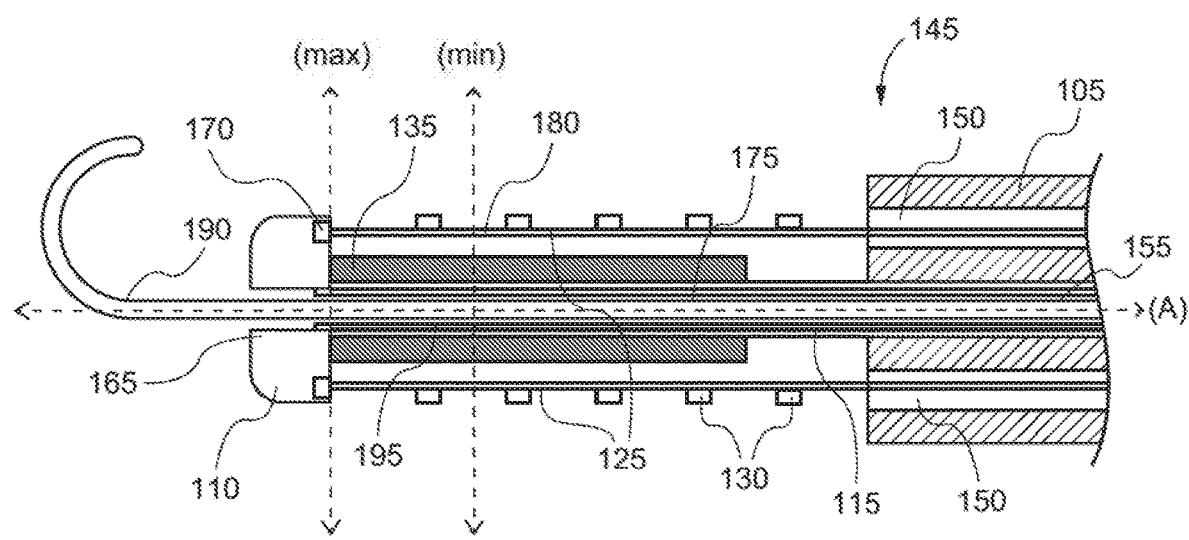
FIG. 1B shows a cross-section of a medical device in accordance with various embodiments.
Figure 1B:
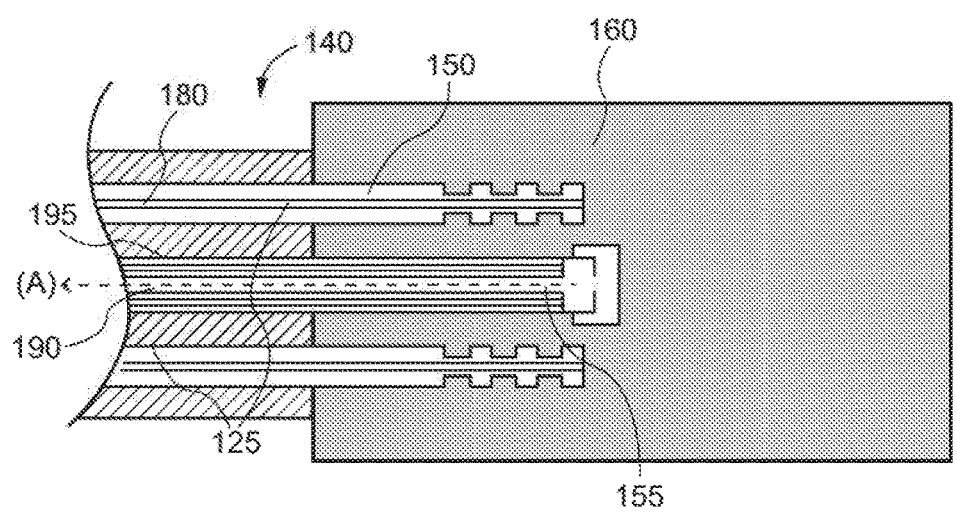
Figure 1C:
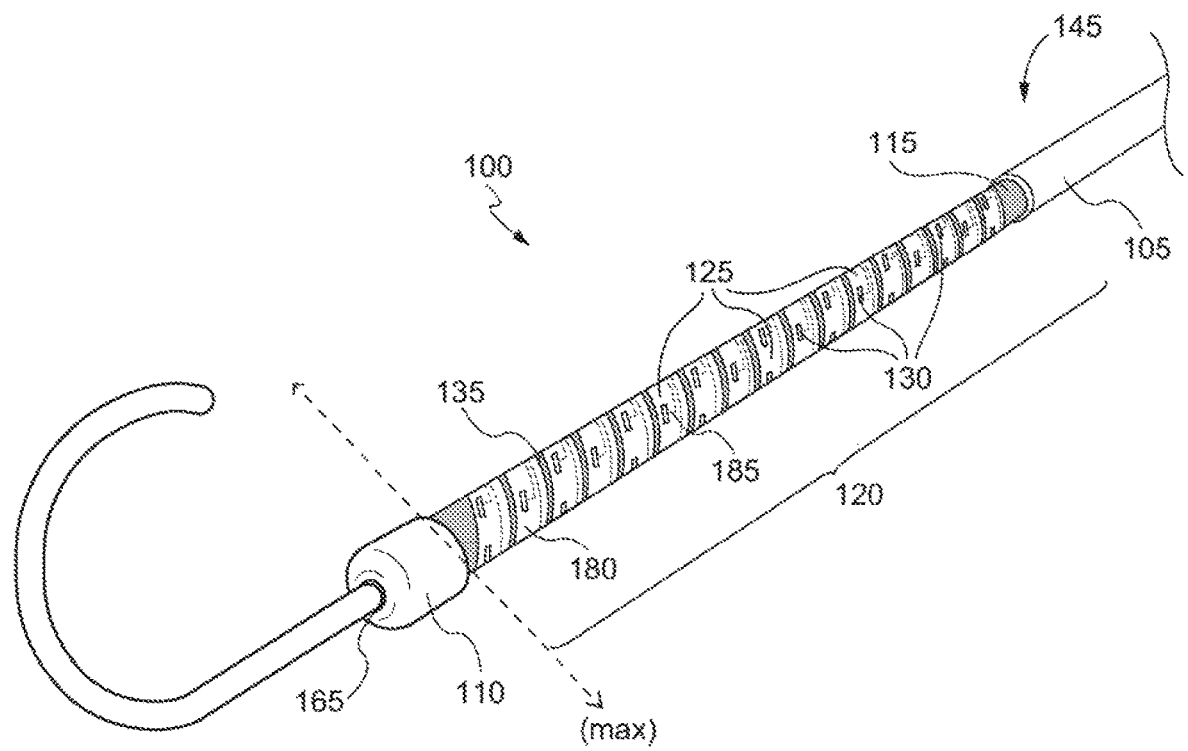
FIG. 1C shows a perspective view of an alternative medical device in accordance with various embodiments.

FIGS. 1A, 1B, and 1C show a medical device 100 in accordance with some aspects of the present invention. In various embodiments, the medical device 100 includes a sheath 105, an end cap 110, and a hollow core 115 extending from the sheath 105 to the end cap 110. The medical device 100 further includes a flexible framework 120 comprising a plurality of thin film elements 125 (e.g, a plurality of longitudinal extending arms) disposed around the hollow core 115. The plurality of thin film elements 125 comprise a plurality of mapping electrodes 130 and optional sensors (not shown). The medical device 105 further includes a travel limiter 135 disposed between the plurality of thin film elements 125 and the hollow core 115.

The sheath 105 may be a shaft or hollow body comprising a proximal end 140, a distal end 145, a channel 150, a lumen 155, and a hub 160 disposed at the proximal end 140. The channel 150 and the lumen 155 may be concentric with a center being the central axis (A) of the sheath 105. The lumen 155 may be in the center of the sheath 105, whereas the channel 150 may be radially a further distance from the central axis (A). In some embodiments, the channel 150 and the lumen 155 are separate tubular structures in the sheath 105 that are not in communication with one another. In other embodiments, the channel 150 and the lumen 155 are tubular structures in the sheath 105 that are in communication with one another. The sheath 105 may be made of an extruded or laminated polymer material. In certain embodiments, the polymer material is silicone rubber, nylon, polyurethane, polyethylene terephthalate (PET), latex, thermoplastic elastomers, or any combination thereof. The hub 160 may be a connection point (e.g., include a connector) for various electronics to the electrodes 130 and optional sensors. The hub 160 may further include a cap that attaches to the hub 160 and occludes the hub 160, the channel 150, and the lumen 155.

The end cap 110 may be a connection point comprising a hole 165 and attachment feature 170 for connection to the flexible framework 120 (see, e.g., FIG. 1B). In some embodiments, the attachment feature 170 is an open/closed structure (e.g., a snap on button) such that the flexible framework 120 is removable from the end cap 110. In other embodiments, the attachment feature 170 is a structure not capable of opening and closing (e.g., a permanent glue or adhesive) such that the flexible framework 120 is irremovable from the end cap 110. Moreover, the end cap 110 may be an end point for the hollow core 115 and the travel limiter 135. In some embodiments, the end cap 110 is integral with the hollow core 115 and/or the travel limiter 135. In additional or alternative embodiments, the end cap 110 is non-integral but attached (removably or irremovably) to the hollow core 115 and/or the travel limiter 135. For example, the end cap 110, hollow core 115, and the travel limiter 135 may be all one monolithic structure. As used herein, the phrase "monolithic" refers to an element or feature fabricated using a same layer of base material. Alternatively, the hollow core 115 and the travel limiter 135 may be a monolithic structure and attached to the end cap 110. Alternatively, the hollow core 115 and the end cap may be a monolithic structure and attached to the travel limiter 135. Alternatively, the end cap 110 and the travel limiter 135 may be a monolithic structure attached to the hollow core 115.

The hollow core 115 may be a shaft or hollow body that fits within the channel 150 of the sheath 105. The hollow core 115 is slidable within the lumen 155 between a maximum extension point (Max) defined by a stopper (not shown) and a minimum extension point (Min) defined by the travel limiter 135. The hollow core 115 includes a lumen 175. In some embodiments, the lumen 175 is in commination with the lumen 155 (see, e.g., FIG. 1B). The hollow core 115 may be made of an extruded or laminated polymer material. In certain embodiments, the polymer material is silicone rubber, nylon, polyurethane, polyethylene terephthalate (PET), latex, thermoplastic elastomers, or any combination thereof.

The plurality of thin film elements 125 are mapping elements for the medical device 100. In some embodiments, the plurality of longitudinal extending arms 125 extend from the proximal end 140 (e.g., connect within the hub 160) through the channel 150 to the end cap 110. The plurality of thin film elements 125 may comprise a supporting structure 180 and a plurality of conductive traces 185 formed on a portion of the supporting structure 180. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 180 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 180 is made of one or more layers of dielectric material formed on a substrate. The substrate may be made from any type of metallic or non-metallic material.

In various embodiments, the one or more conductive traces 185 are a plurality of traces, for example, two or more conductive traces or from two to twenty-four conductive traces. The plurality of conductive traces 185 electrically connect each of the plurality of mapping electrodes 130 to one or more conductive contacts in the hub 160. The plurality of mapping electrodes 130 and/or the plurality of conductive traces 185 are comprised of one or more layers of conductive material. The conductive material selected for the plurality of mapping electrodes 130 and/or one or more conductive traces 185 should have biocompatibility, good electrical conductivity, and may include pure metals, metal alloys, combinations of metals and dielectrics, and the like. For example, the conductive material may be platinum (Pt), platinum/iridium (Pt/Tr), titanium (Ti), gold/titanium (Au/Ti), or any alloy thereof. In some embodiments, it is also desirable that the conductive material selected for the plurality of mapping electrodes 130 and/or one or more conductive traces 185 have thermal expansion characteristics or a coefficient of thermal expansion (CTE) that is approximately equal to that of CTE of the supporting structure 180. Matching the CTE of components that contact one another is desirable because it eliminates the development of thermal stresses, which may occur during fabrication and the operation of the flexible framework 120, and thus eliminates a known cause of mechanical failure in the components. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

In various embodiments, the medical device 100 may further comprise a guide wire 190 disposed in the sheath 105 and extending from the opening 165 in the end cap 110 (see, e.g., FIG. 1B). The guide wire 190 may extend through the lumen 155 and the lumen 175. In certain embodiments, the guide wire 190 has a "J" shaped distal end to avoid trauma to the biological system during insertion of the guide wire 190 and the medical device 100. In some embodiments, the medical device 100 may further comprise a pull cable 195 disposed in the sheath 105 and attached to the end cap 110 or the hollow core 115. In some embodiments, the pull cable 195 extends from the proximal end 140 (e.g., connect within the hub 160) through the lumen 155 to the end cap 110 or the hollow core 115. Tension may be provided on the pull cable 195 for retracting the hollow core 115 and anchoring the travel limiter 135 to the distal end 145 of the sheath 105.

FIG. 1A shows a first configuration of the plurality of thin film elements 125 disposed around the hollow core 115. The first configuration is for insertion of the medical device 100 into the biological system prior to mapping a cavity of the biological system. In the first configuration, the hollow core 115 is extended to its maximum extension point (Max) defined by the stopper (not shown). The travel limiter 135 is structured to limit the distance that the end cap 110 and the hollow core 115 can be retracted in direction parallel to the central axis (A) towards the proximal end 140 of the sheath 105 as the medical device 100 transforms from the first configuration to a second configuration. In the first configuration, the travel limiter 135 is extended with the hollow core 115 to the maximum extension point (Max). At the maximum extension point (Max), the travel limiter 135 may cover between 50% and 85%, for example, approximately 75%, of the total length of the hollow core 115 between the distal end 145 of the sheath 105 to the end cap 110. In some embodiments, in the first configuration each thin film element 125 of the plurality of thin film elements 125 extends from the distal end 145 of the sheath 105 to the end cap 110 in a straight line parallel to the central axis (A) of the sheath 105 and hollow core 115. In other words, the plurality of thin film elements 125 are drawn taught in straight lines over the hollow core 115 due to the hollow core 115 being extended to is maximum extension point (Max).

FIG. 1C shows an alternative first configuration of the plurality of thin film elements 125 disposed around the hollow core 115. In some embodiments, in the alternative first configuration, each thin film element 125 of the plurality of thin film elements 125 extends from the distal end 145 of the sheath 105 to the end cap 110 in a helix around the central axis (A) of the sheath 105 and hollow core 115. In other words, the plurality of thin film elements 125 are drawn taught in a helical pattern over the hollow core 115 due to the hollow core 115 being extended to is maximum extension point (Max).

Figure 2A:
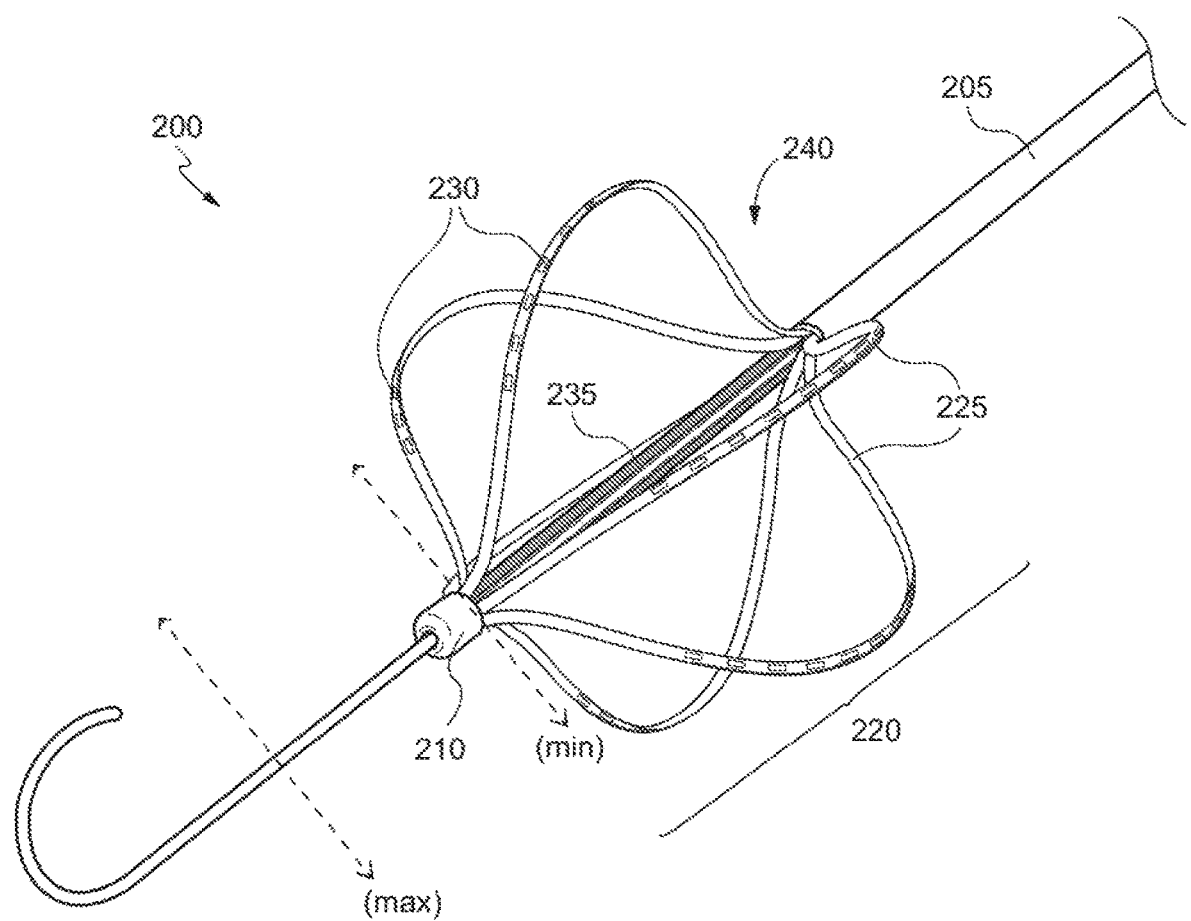
FIG. 2A shows a perspective view of a medical device in accordance with various embodiments.
Figure 2B:
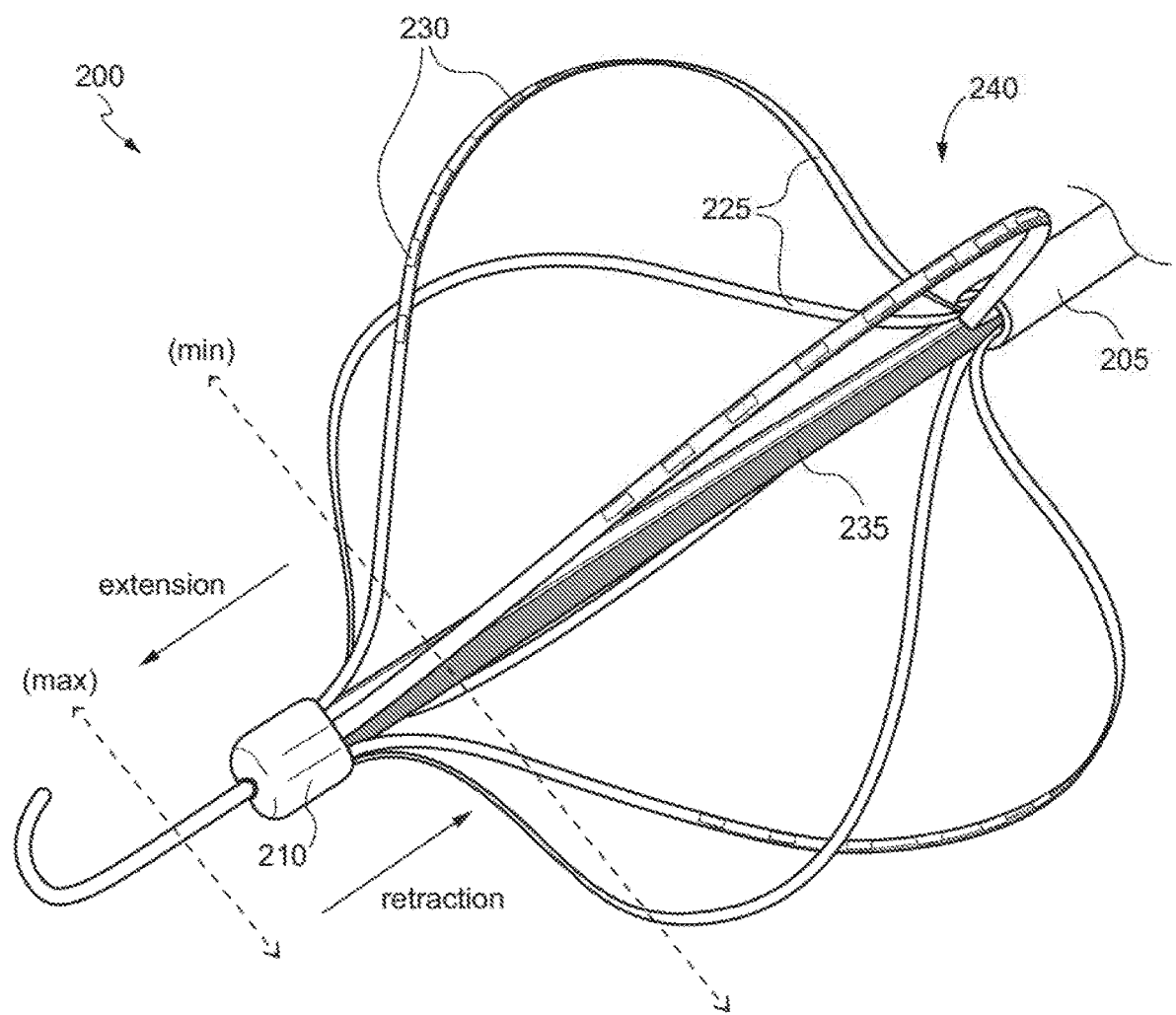
FIG. 2B shows a detailed perspective view of a medical device in accordance with various embodiments.
Figure 2C:
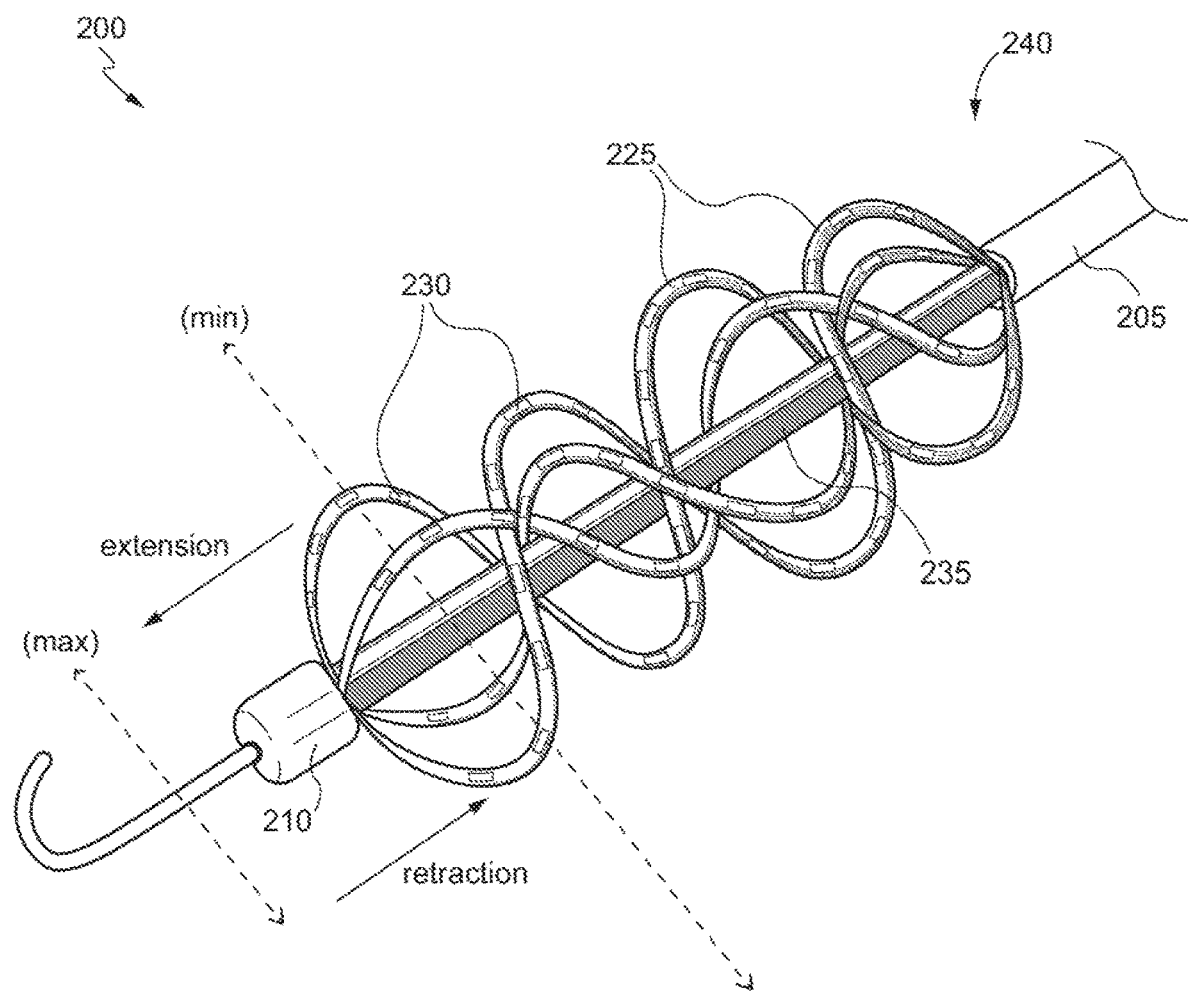
FIG. 2C shows a detailed perspective view of an alternative medical device in accordance with various embodiments.

FIGS. 2A, 2B, and 2C show a medical device 200 (e.g., the medical device 100 described with respect to FIGS. 1A, 1B, and 1C) in accordance with some aspects of the present invention. In various embodiments, the medical device 200 includes a sheath 205, an end cap 210, and a hollow core (not shown because it is disposed under the travel limiter 235 and partially retracted into the lumen of the sheath 205) extending from the sheath 205 to the end cap 210. The medical device 200 further includes a flexible framework 220 comprising a plurality of thin film elements 225 (e.g., a plurality of longitudinal extending arms) disposed around the hollow core. The plurality of thin film elements 225 comprise a plurality of mapping electrodes 230 and optional sensors (not shown). The medical device 205 further includes a travel limiter 235 disposed between the plurality of thin film elements 225 and the hollow core.

FIGS. 2A and 2B show the second configuration of the thin film elements 225 disposed around the hollow core. The second configuration is for sensing and mapping electrical activity on a three-dimensional model of the biological system. In the second configuration, the hollow core is retracted to its minimum extension point (Min) defined by the travel limiter 235 (tension is provided on the pull cable). As described herein, the travel limiter 235 is a structure configured to limit the distance that the end cap 210 and the hollow core can be retracted in direction parallel to the central axis (A) towards the proximal end 240 of the sheath 105. In the second configuration, the travel limiter 235 is retracted, with the hollow core to the minimum extension point (Min). At the minimum extension point (Min), the travel limiter 235 covers 100% of the total length of the hollow core between the distal end 245 of the sheath 205 to the end cap 210. In some embodiments, in the second configuration, each thin film element 225 of the plurality of thin film elements 225 moves in a radial direction from hollow core and the central axis (A). In other words, the plurality of thin film elements 225 pop open over the hollow core due to the hollow core being retracted to is minimum extension point (Min). In some embodiments, each thin film element 225 of the plurality of thin film elements 225 take on a bell shaped curve.

FIG. 2C shows an alternative second configuration of the plurality of longitudinal extending arms 225 disposed around the hollow core 215. In some embodiments, in the alternative second configuration, each thin film element or extending arm 225 of the plurality of longitudinal extending arms 225 moves in a radial direction from hollow core and the central axis (A). In other words, the plurality of longitudinal extending arms 225 pop open over the hollow core due to the hollow core being retracted to is minimum extension point (Min). In some embodiments, each thin film element or extending arm 225 of the plurality of longitudinal extending arms 225 take on a coil shape comprising end portions and a center. In certain embodiments, the end portions have a smaller radius than a radius of the central portion.

Figure 3A:
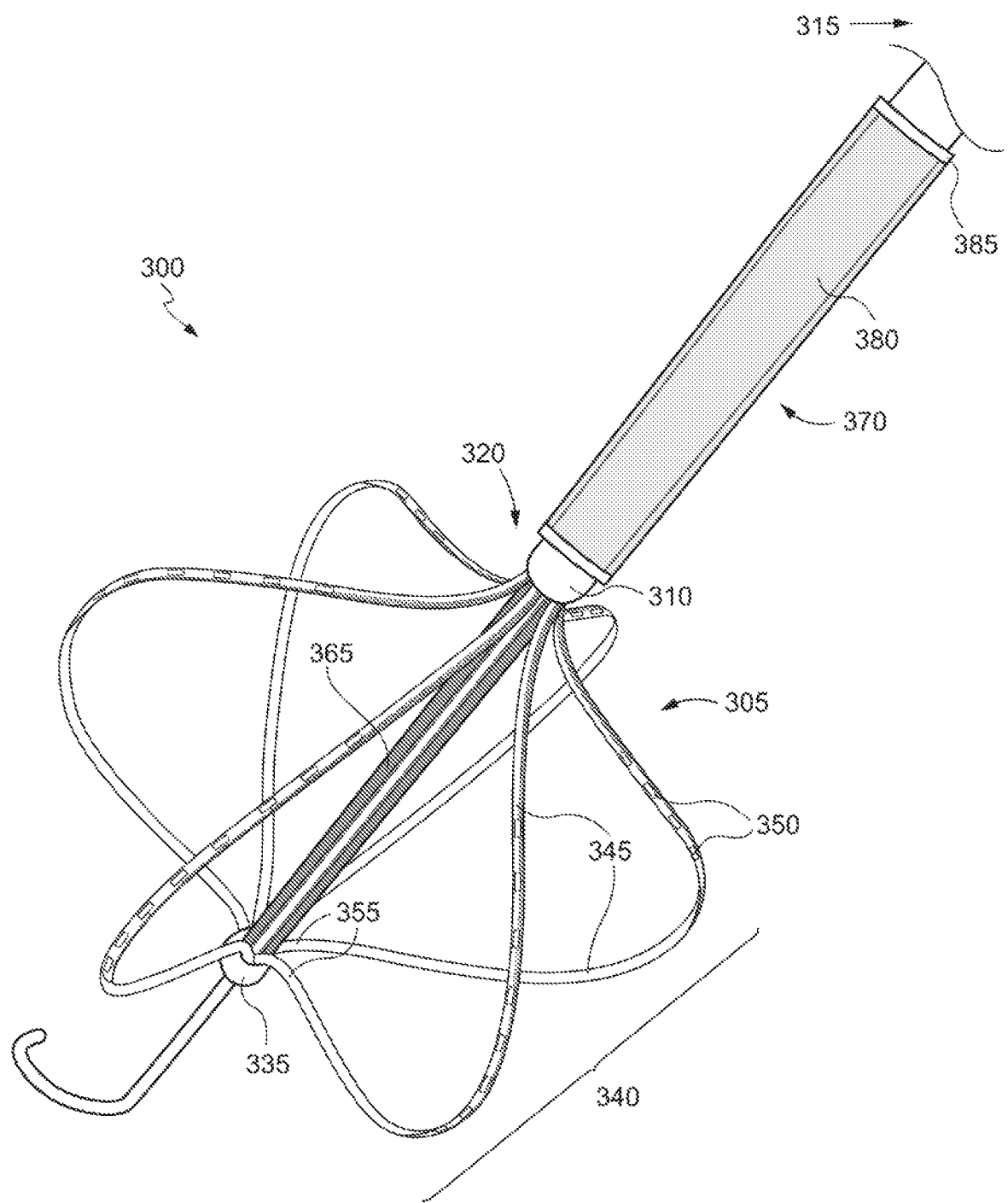
FIG. 3A shows a perspective view of a medical system in accordance with various embodiments.
Figure 3B:
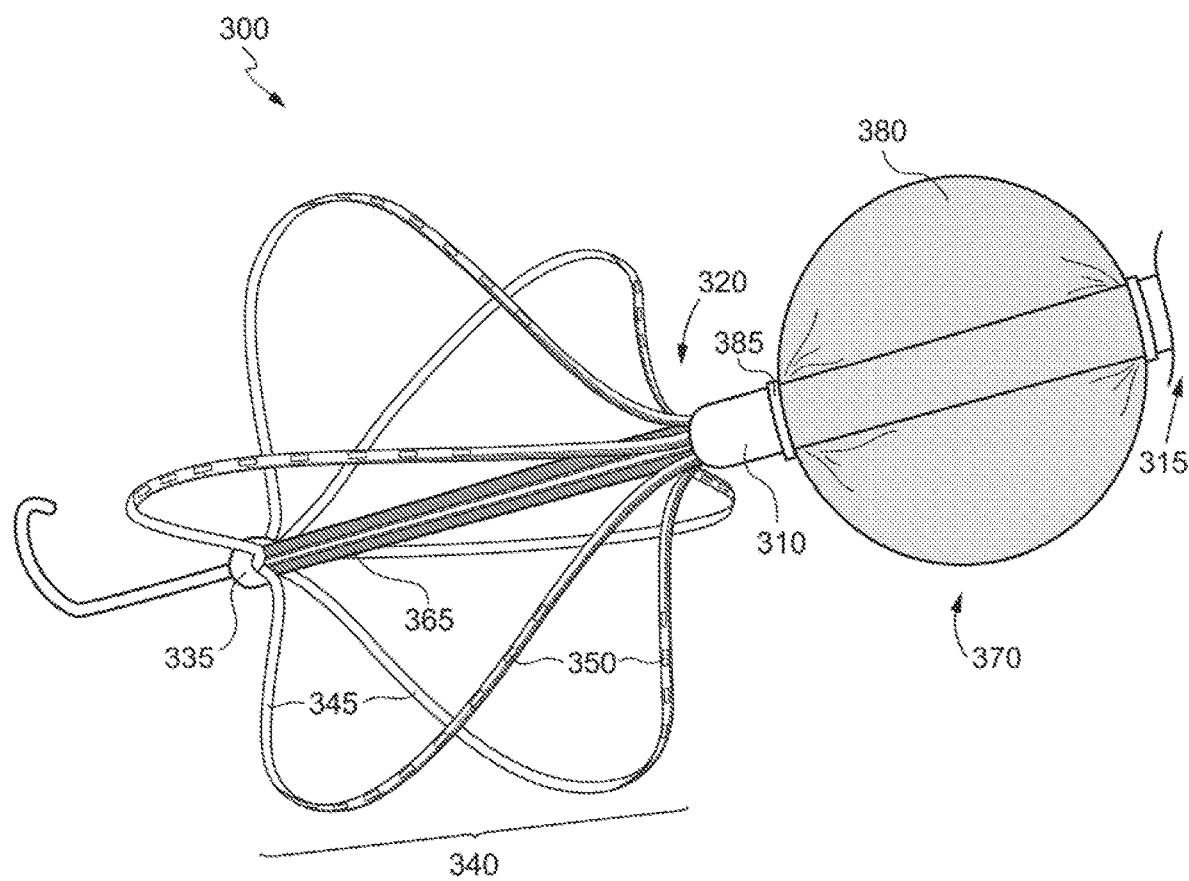
FIG. 3B shows a perspective view of a medical system in accordance with various embodiments.

FIGS. 3A and 3B show a medical system 300 in accordance with some aspects of the present invention. The medical system 300 comprises a mapping catheter 305 (e.g., the medical device 100/200 described with respect to FIGS. 1A, 1B 1C, 2A, 2B, and 2C) comprising a sheath 310 having a proximal end 315, a distal end 320, a channel, and a hub disposed at the proximal end 315. The mapping catheter 305 further comprises an end cap 335 and a hollow core extending from the distal end 320 of the sheath 310 to the end cap 335. The mapping catheter 305 further comprises a flexible framework 340 comprising a plurality of thin film elements 345 disposed around the hollow core. The plurality of thin film elements 345 comprise a plurality of mapping electrodes 350, distal ends 355 of the plurality of thin film elements 345 are attached to the end cap 335, the plurality of thin film elements 345 extend through the channel of the sheath 310, and proximal ends of the plurality of thin film elements 345 are attached to the hub. The mapping catheter 305 further comprises a travel limiter 365 attached to the end cap 335 and disposed between the plurality of thin film elements 345 and the hollow core.

In various embodiments, the medical system 300 further comprises a treatment catheter 370 disposed over at least a portion of the mapping catheter 305. For example, the treatment catheter 370 may be disposed over the sheath 310. Additionally, (for example upon completion of mapping) the treatment catheter 370 may slide over the hollow core 365 and/or beyond the distal ends 355 of the plurality of longitudinal extending aims 345, if required. In some embodiments, the treatment catheter 370 is a cryoballoon catheter comprising a cryoballoon 380 disposed over a hollow body 385, and the hollow body 385 is disposed over the sheath 310 of the mapping catheter 305. FIG. 3A shows the cryoballoon 380 deflated and FIG. 3B shows the cryoballoon 380 inflated. In other embodiments, the treatment catheter 370 is an ablation catheter comprising radiofrequency electrodes disposed over a hollow body, and the hollow body is disposed over the sheath 310 of the mapping catheter 305.

III. Methods of Deploying Dual Catheter Devices and Systems

Figure 4:
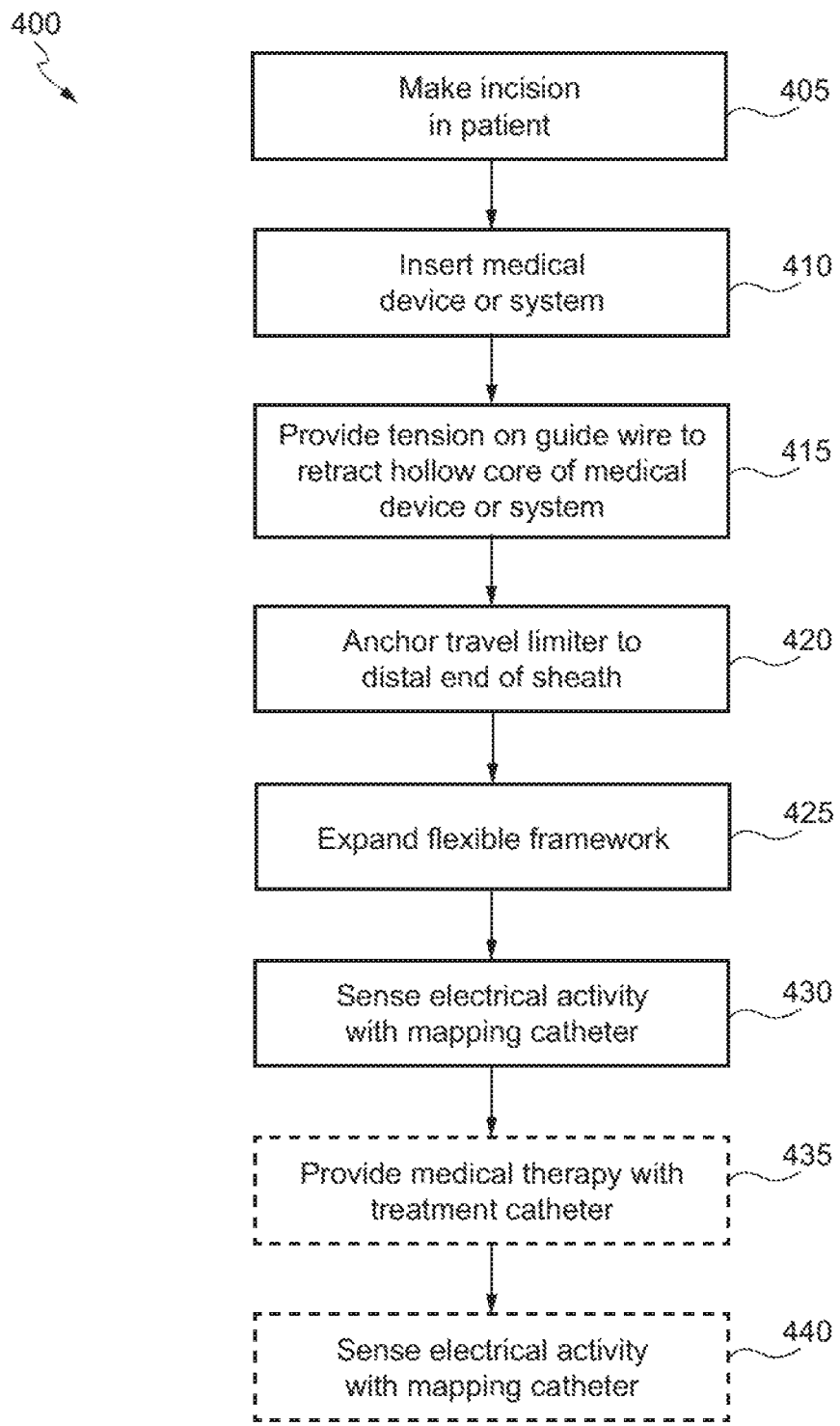
FIG. 4 shows a flow diagram of a process for using a medical device or system in accordance with various embodiments.

FIG. 4 depicts a simplified flowchart depicting processing performed accessing a site of a target biological structure in a patient and delivering a medical device or system for mapping and optionally medical therapy of the site of the target biological structure according to various embodiments. As noted herein, the flowchart of FIG. 4 illustrates the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented manually by a user such as a surgeon or by special purpose hardware-based systems that perform the specified functions or acts, or combinations of special purpose hardware and computer instructions.

FIG. 4 depicts a simplified flowchart 400 illustrating a process used by user to access, map, and optionally provide treatment to a site of a target biological structure in a patient. In some embodiments, the site of the target biological structure is accessed using the medical devices or systems described with respect to FIGS. 1A, 1B 1C, 2A, 2B, 2C, 3A, and 3B. At step 405, one or more incisions are made in a patient to access a target biological structure. At step 410, the medical device or system is inserted and/or guided into a cavity of a body through the one or more incisions to a target site of the biological system. In some embodiments, the medical device is a mapping catheter. In some embodiments, the medical system includes a mapping catheter and optionally a treatment catheter. The mapping catheter includes a sheath, an end cap, and a hollow core extending from the sheath to the end cap. The mapping catheter further includes a flexible framework comprising a plurality of longitudinal extending arms (e.g., a plurality of thin film elements) disposed in a first configuration around the hollow core. The plurality of longitudinal extending aims comprise a plurality of mapping electrodes and optional sensors (not shown). In some embodiments, in the first configuration, each thin film element or extending arm of the plurality of longitudinal extending arms extends from the distal end of the sheath to the end cap in a straight line parallel to the central axis (A) of the sheath and hollow core. In other embodiments, in the first configuration, each thin film element or extending aim of the plurality of longitudinal extending arms extends from the distal end of the sheath to the end cap in a helix around the central axis (A) of the sheath and hollow core. The mapping catheter further includes a travel limiter disposed between the plurality of longitudinal extending arms and the hollow core.

At step 415, tension is provided on a pull cable to retract the end cap towards a distal end of the sheath and retract the hollow core within the sheath. At step 420, the travel limiter is anchored to the distal end of the sheath. The anchoring can be provided by the pressure exerted by tension in the pull cable on the travel limiter against the distal end of the sheath. Optionally, the anchoring, may further include an anchor structure on the travel limiter that engages a corresponding anchor structure at the distal end of the sheath (e.g., a clip). At step 425, the plurality of thin film elements are expanded to a second configuration. In some embodiments, in the second configuration, each thin film element or extending arm of the plurality of longitudinal extending arms moves in a radial direction from hollow core and the central axis (A). In some embodiments, each thin film element or extending arm, of the plurality of longitudinal extending arms take on a bell shaped curve. In other embodiments, in the second configuration, each thin film element or extending arm of the plurality of longitudinal extending arms moves in a radial direction from hollow core and the central axis (A). In some embodiments, each thin film element or extending arm of the plurality of longitudinal extending arms take on a coil shape comprising end portions and a center. In certain embodiments, the end portions have a smaller radius than a radius of the central portion.

At step 430, the mapping catheter is used to sense electrical activity at a site within the cavity and map the activity on a three-dimensional model of the biological system. At optional step 435, a treatment catheter is deployed over at least a portion of the mapping catheter to provide medical therapy (e.g., cryoablation) to the site within the cavity of the body based at least on the activity mapped on the three-dimensional model of the biological system. At optional step 440, the mapping catheter is used to sense electrical activity at the site within the cavity to confirm whether the medical therapy was successful. As should be understood, one or more of steps 415, 420, 425, 430, 435, and 440 can be performed sequentially or simultaneously.

IV. Integrated Catheter Devices and Systems

FIGS. 5A-5I show a medical device 500 in accordance with some aspects of the present invention. In various embodiments, the medical device 500 includes a sheath 505, a balloon 510 disposed over at least a portion of the sheath 505 and a flexible framework 515 comprising an expandable region 520 and a non-expandable region 525. The expandable region 520 comprises a plurality of longitudinal extending arms 530 (e.g., splines or thin film elements as discussed with respect to FIGS. 1A, 1B 1C, 2A, 2B, 2C, 3A, and 3B). Each arm of the plurality of longitudinal extending arms 530 comprises one or more layers of dielectric material 535, one or more conductive traces 540, and one or more electrodes 545 electrically connected to the one or more conductive traces 540, where the expandable region 520 is formed on an inflatable portion of the balloon 510. The non-expandable region 525 comprises one or more layers of dielectric material 550, the one or more conductive traces 540, and one or more contacts 555 electrically connected to the one or more conductive traces 540, where the non-expandable region 525 is formed on a non-inflatable portion of the balloon 510 or the sheath 505. The medical device 500 further includes a cable 560 comprising a plurality of wires electrically connected to the one or more contacts 555.

Figure 5A:
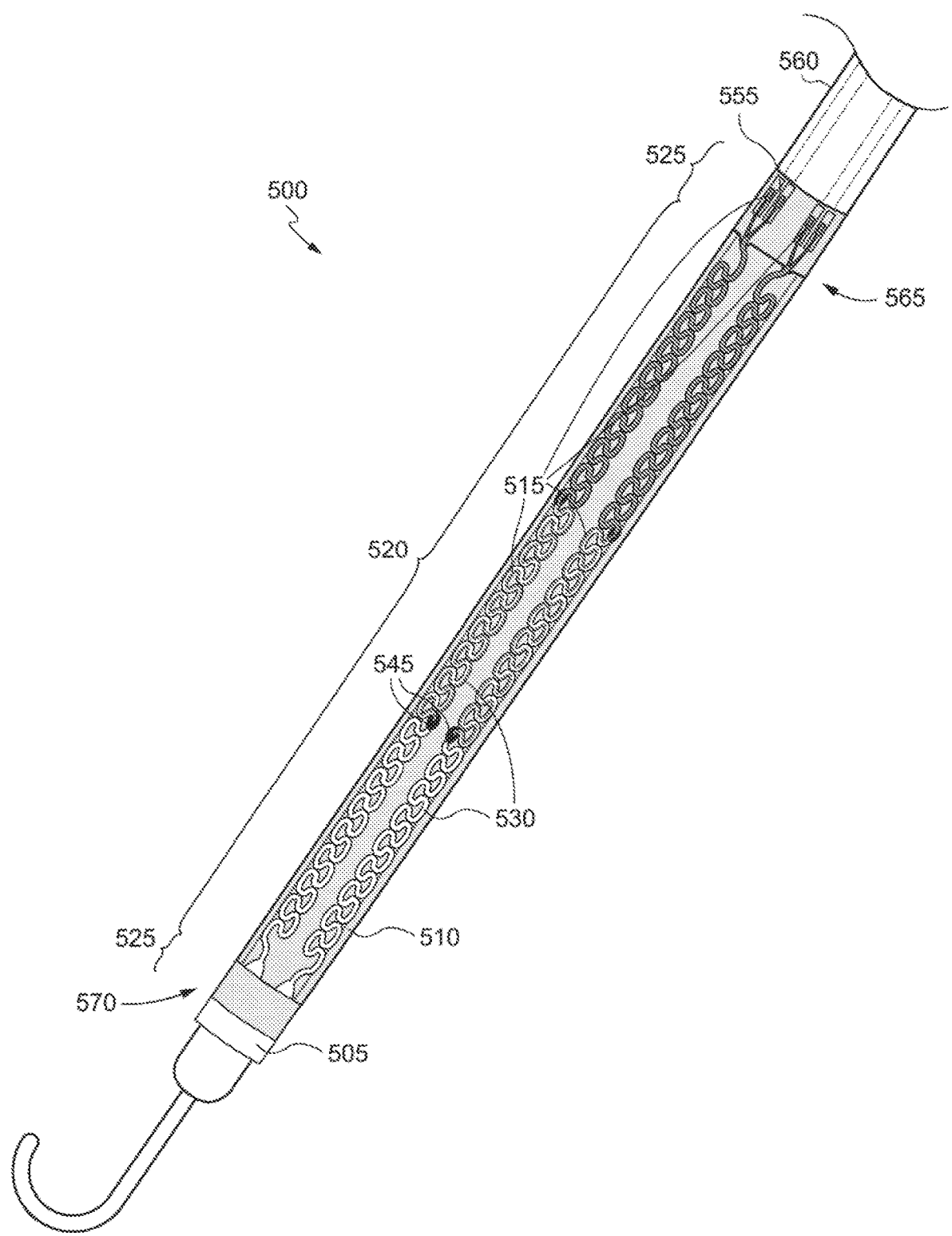
FIG. 5A shows a perspective view of a medical device in a deflated configuration in accordance with various embodiments.
Figure 5B:
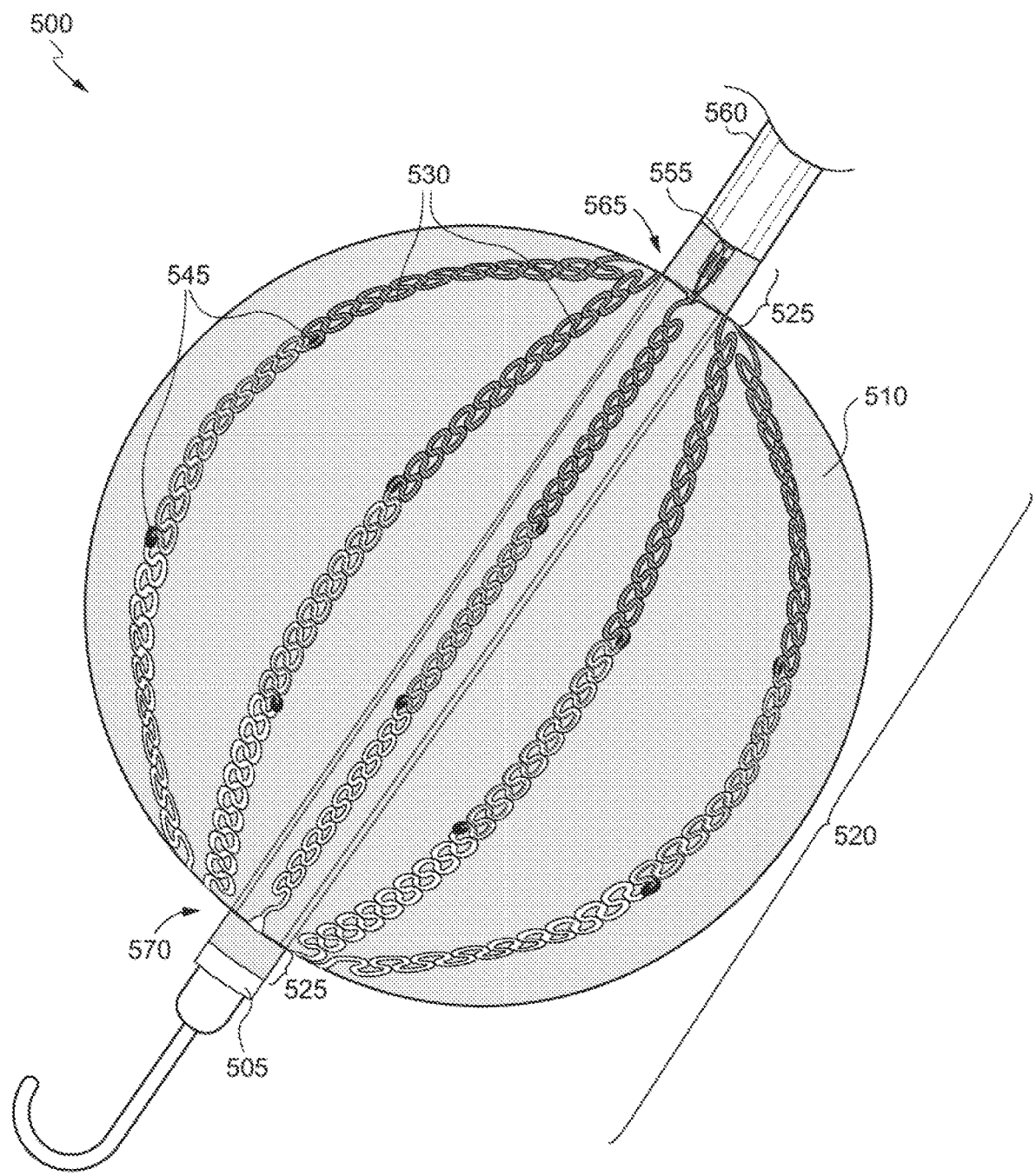
FIG. 5B shows a perspective view of a medical device in an inflated configuration in accordance with various embodiments.

As shown in FIGS. 5A and 5B, the plurality of longitudinal extending arms 530 may extend from a proximal end 565 of the balloon 510 to a distal end 570 of the balloon 510. In some embodiments, a length of the arms 530 equals approximately half of a perimeter of the balloon 510 in an inflated state. In certain embodiments, the length of the arms is between 20 mm and 100 mm, for example about 36 mm. The one or more electrodes 545 may be distributed on the arms 530 in an arbitrary or in a predetermined pattern. For example, each of the arms 530 may comprise two or more electrodes 545 disposed in a northern hemisphere region of the balloon 510 (between the mid-point of the balloon 510 and the distal end 570). Alternatively, each of the arms 530 may comprise two or more electrodes 545 disposed in a southern hemisphere region of the balloon 510 (between the mid-point of the balloon 510 and the proximal end 565). Alternatively, each of the arms 530 may comprise two or more electrodes 545 disposed across the northern hemisphere region and the southern hemisphere region of the balloon 510. Alternatively, each of the arms 530 may comprise two or more electrodes 545 disposed in a central region of the balloon 510 (near the mid-point of the balloon 510). In some embodiments, any number of the electrodes 545 are replaced with one or more sensors (e.g., pressure or temperature sensors).

Figure 5C:
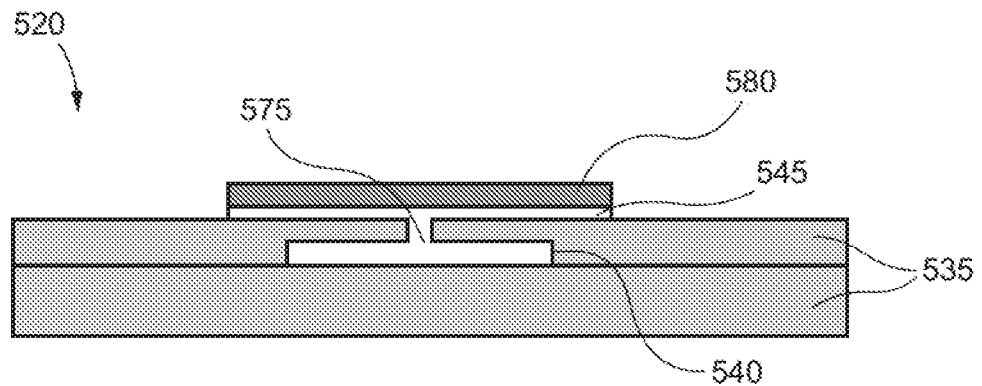
FIG. 5C shows cross-section of an expandable region in accordance with various embodiments.

FIG. 5C shows a cross section of the expandable region 520 fabricated in accordance with aspects of the present disclosure. In various embodiments, each arm of the plurality of longitudinal extending arms 530 comprises the one or more conductive traces 540 formed between the layers of dielectric material 535 and the one or more electrodes 545 formed on a top surface of the layers of dielectric material 535 (the exposed surface of the top layer of dielectric material). The one or more layers of dielectric material 535 may be formed in the shape of a structure (e.g. a serpentine as shown in FIGS. 5A, 5B, and 5E) that allows for the flexible framework 515 to be expanded, contracted, opened, or closed in order to position the flexible framework 515 on the balloon 510 and allows the flexible framework 515 to move (e.g., expand or contract) with inflation and deflation of the balloon 510. In various embodiments, the one or more layers of dielectric material 535 comprise a polymer of imide monomers, a liquid crystal polymer (LCP), parylene, polyether ether ketone (PEEK), or any combination thereof. In certain embodiments, the one or more layers of dielectric material 535 comprise a polymer of imide monomers (i.e., a polyimide) or a liquid crystal polymer (LCP) such as Kevlar®.

The one or more conductive traces 540 may be comprised of one or more layers of conductive material. The conductive material selected for the one or more conductive traces 540 should have biocompatibility, good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. The one or more electrode 545 may be comprised of one or more layers of conductive material. The conductive material selected for the one or more electrodes 545 should have biocompatibility, good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof.

The arms 530 may further comprise one or more contacts or vias 575 formed between the layers of dielectric material 535 that provides the electrical contact between one or more electrodes 545 and the one or more conductive traces 540. The one or more contacts or vias 575 may be comprised of conductive material such as platinum (Pt), platinum/iridium (Pt/Ir), titanium (Ti), gold/titanium (Au/Ti), or any alloy thereof. The arms 530 may further comprise a low-impedance material coating or overmold 580 formed over the layers of dielectric material 535 and/or the one or more electrodes 545. Materials that may be considered low impedance include polymers, foams, biological materials, and composites.

Figure 5D:
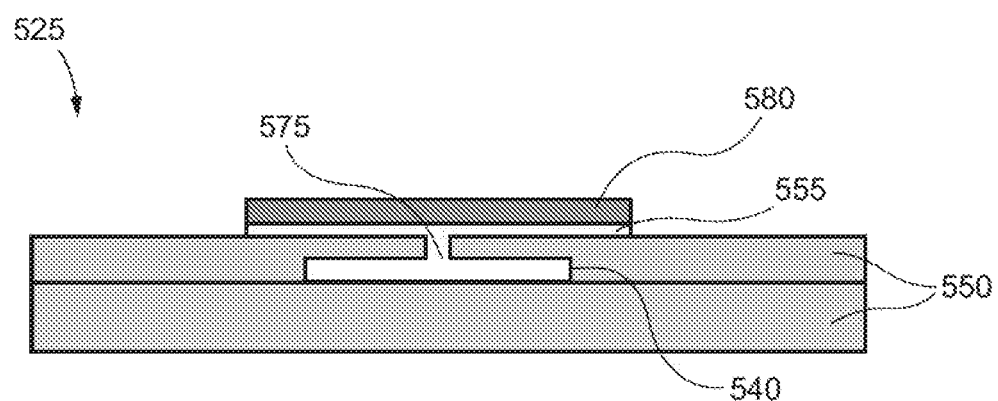
FIG. 5D shows cross-section of an non-expandable region in accordance with various embodiments.
Figure 5E:
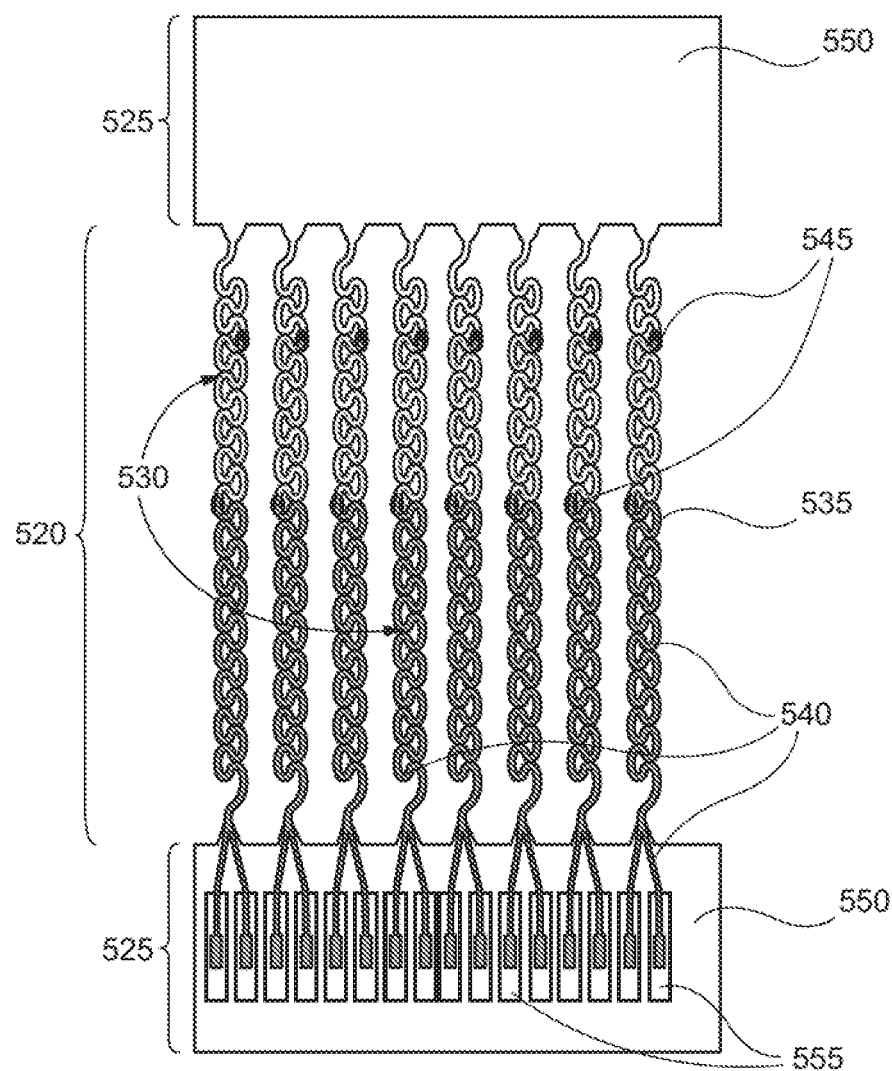
FIG. 5E shows a top planar view of an expandable region and non-expandable region of a flexible framework in accordance with various embodiments.

FIG. 5D shows a cross section of the non-expandable region 525 fabricated in accordance with aspects of the present disclosure. In various embodiments, the non-expandable region 525 comprises the one or more conductive traces 540 formed between the layers of dielectric material 550 and the one or more contacts 555 formed on a top surface of the layers of dielectric material 550 (the exposed surface of the top layer of dielectric material). The one or more layers of dielectric material 550 may be formed in the shape of a structure (e.g., a column) that allows for the flexible framework 515 to support microelectronic structures including the one or more conductive traces 540 and the one or more contacts 555 for connection of the one or more electrodes 545 to a hub, controller, and/or electronics module. In various embodiments, the one or more layers of dielectric material 550 comprise the same material as the one or more layers of dielectric material 535, for example, a polymer of imide monomers, a liquid crystal polymer (LCP), parylene, polyether ether ketone (PEEK), or any combination thereof. In some embodiments, the one or more layers of dielectric material 550 may comprise additional or a different material from that of the one or more layers of dielectric material 535, for example, a polymer of imide monomers, a liquid crystal polymer (LCP), parylene, polyether ether ketone (PEEK), thermoplastic polyurethane (TPU), other thermoset plastics such as epoxies, polyesters, silicones, and phenolics, or any combination thereof.

The one or more conductive traces 540 may be comprised of one or more layers of conductive material. The conductive material selected for the one or more conductive traces 540 should have biocompatibility, good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. The one or more contacts 555 may be comprised of one or more layers of conductive material. The conductive material selected for the one or more contacts 555 should have biocompatibility good electrical conductivity, and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof.

The non-expandable region 525 may further comprise one or more contacts or vias 575 formed between the layers of dielectric material 550 that provides the electrical contact between one or more contacts 555 and the one or more conductive traces 540. The one or more contacts or vias 575 may be comprised of conductive material such as platinum (Pt), platinum/iridium (PO), titanium (Ti), gold/titanium (Au/Ti), or any alloy thereof. The non-expandable region 525 may further comprise a low-impedance material coating or overmold 580 formed over the layers of dielectric material 550 and/or the one or more contacts 555. Materials that may be considered low impedance include polymers, foams, biological materials, and composites.

Figure 5F:
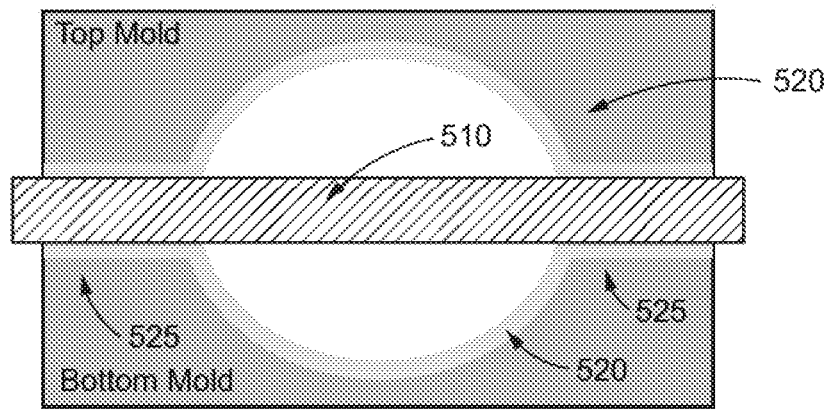
FIGS. 5F and 5G show a process for manufacturing a medical device in accordance with various embodiments.
Figure 5G:
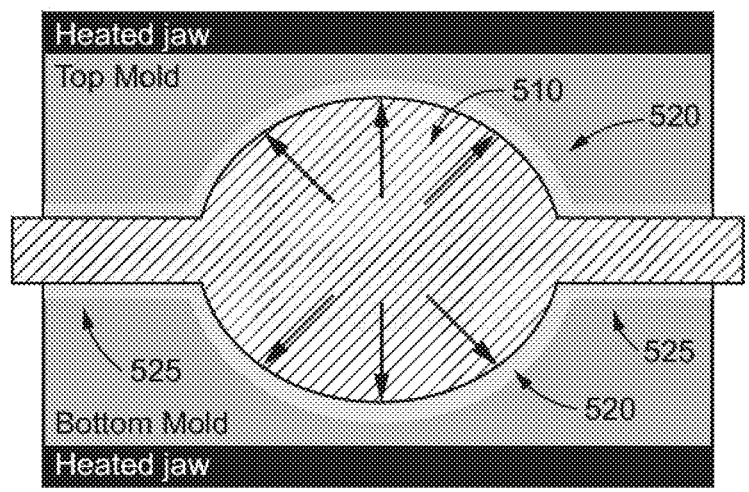

FIG. 5E shows a top planar view of the flexible framework 515 prior to integration with the balloon 510. Each arm 530 has patterned conductive traces 540 (serpentine) and one or more electrodes 545 on one or more layers of dielectric material 535 (springs) for stretchability. The arms 510 may be glued and embedded on the balloon 510 during blow molding as shown in FIGS. 5F and 5G. Initially, the flexible framework 515 planar structure (shown in FIG. 5E) may be rolled and inserted into a mold. A tube of the one or more layers of material to be used to fabricate the balloon 510 is also inserted into the mold. The one or more layer of material for the balloon may include polyurethane, polycarbonate, silicone, polyethylene, fluoropolymer and/or other medical polymers, copolymers and combinations or blends. In certain embodiments, the balloon 510 is comprised of one or more layer of polyurethane. As shown in FIG. 5F, the mold may be heated such that the one or more non-expandable regions 525 are embedded into end portions of the tube of the one or more layers of material. As shown in FIG. 5G, the tube of the one or more layers of material may be expanded to form the balloon 510 and the mold may be heated such that the expandable region 520 is embedded into the balloon 510.

Figure 5H:
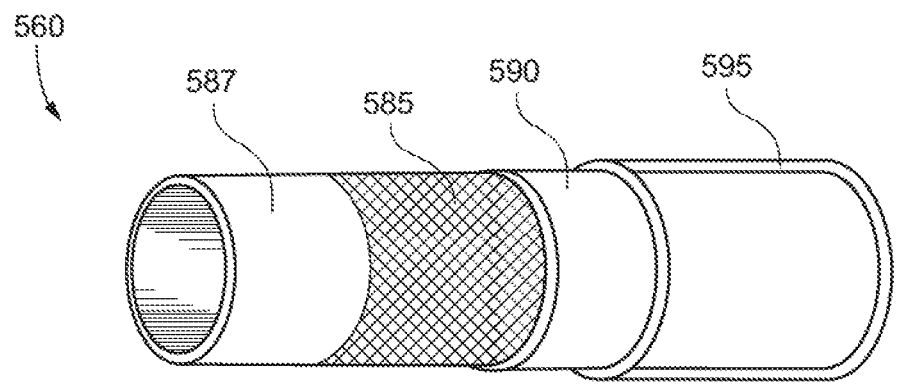
FIG. 5H shows a cable in accordance with various embodiments.

FIG. 5H shows the cable 560 comprising a plurality of wires 585, which can be electrically connected to the one or more contacts 555. In various embodiments, the cable 560 is run through a channel or lumen of the sheath 505. In other embodiments, the cable 560 is integrated with the sheath 505, for example, the cable 560 forms a portion of the sheath 505. In some embodiments, the wires 585 are formed as a braided structure disposed between one or more layers of dielectric material. Alternatively, the wires 585 may be provided as a multifilar MP35N cable in a multi-lumen tubing. In some embodiments, the wires 585 are stainless steel wire having a thickness between 25 μm and 250 μm, for example about 50 μm. The one or more layers of dielectric material may include a first polymer layer 587 such as a polytetrafluoroethylene (PTFE) liner used to create a flexible shaft for the cable 560 and support for the wires 585. The one or more layers of dielectric material may further include a second polymer layer 590 such as a thermoplastic elastomer (e.g. Pebax®) or polyamide (e.g., Nylon) used to encapsulate the wires 585. The one or more layers of dielectric material may further include a third polymer layer 595 such as a heath shrink material (e.g., FluoroPEELZ®) used to define an outer diameter of the cable 560, reflow the second polymer layer 590, and reflow the layers of dielectric material 550 for bonding.

Figure 5I:
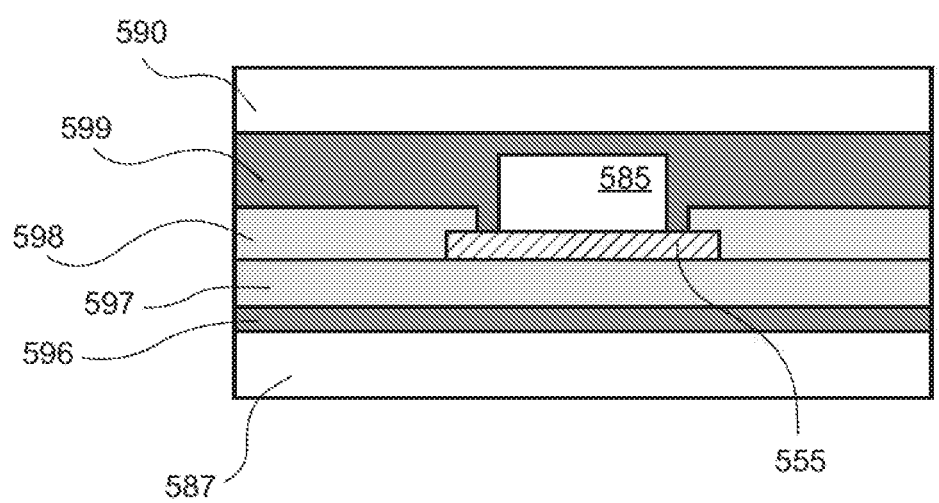
FIG. 5I shows a cross-section of a bonding site between the flexible framework and the cable in accordance with various embodiments.

FIG. 5I shows a cross section at a bonding site showing how the layers of dielectric material 550 may be used as a non-conductive adhesive for bonding or integrating the non-expandable region 525 with the cable 560 in accordance with aspects of the present disclosure. In some embodiments, the one or more layers of dielectric material 550 comprise a first polymer layer 596 or backing such as a thermoplastic polyurethane layer, a second polymer layer 597 such as polyimide support the one or more contacts 555, a third polymer layer 59S such as polyimide to partially cover the one or more electrodes 545, and a fourth polymer layer 599 such as a thermoplastic polyurethane layer to cover the wire 585 (positioned in electrical contact with the contact 555). At the bonding site, the one or more layers of dielectric material 550 may be encapsulated between the first polymer layer 587 and the second polymer layer 590 of the cable 560.

Figure 6A:
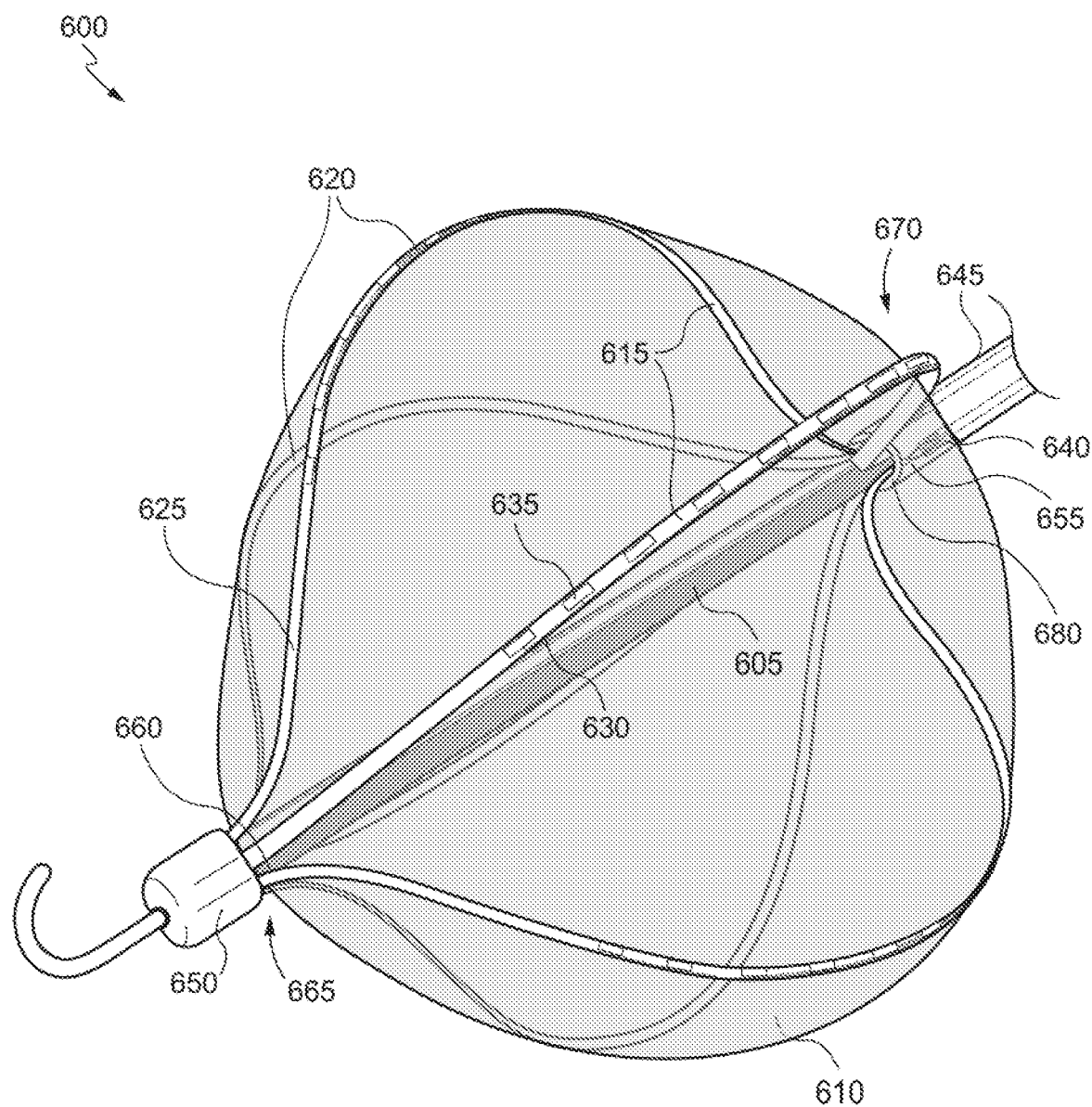
FIG. 6A shows a perspective view of an alternative medical device in an inflated configuration in accordance with various embodiments.
Figure 6B:
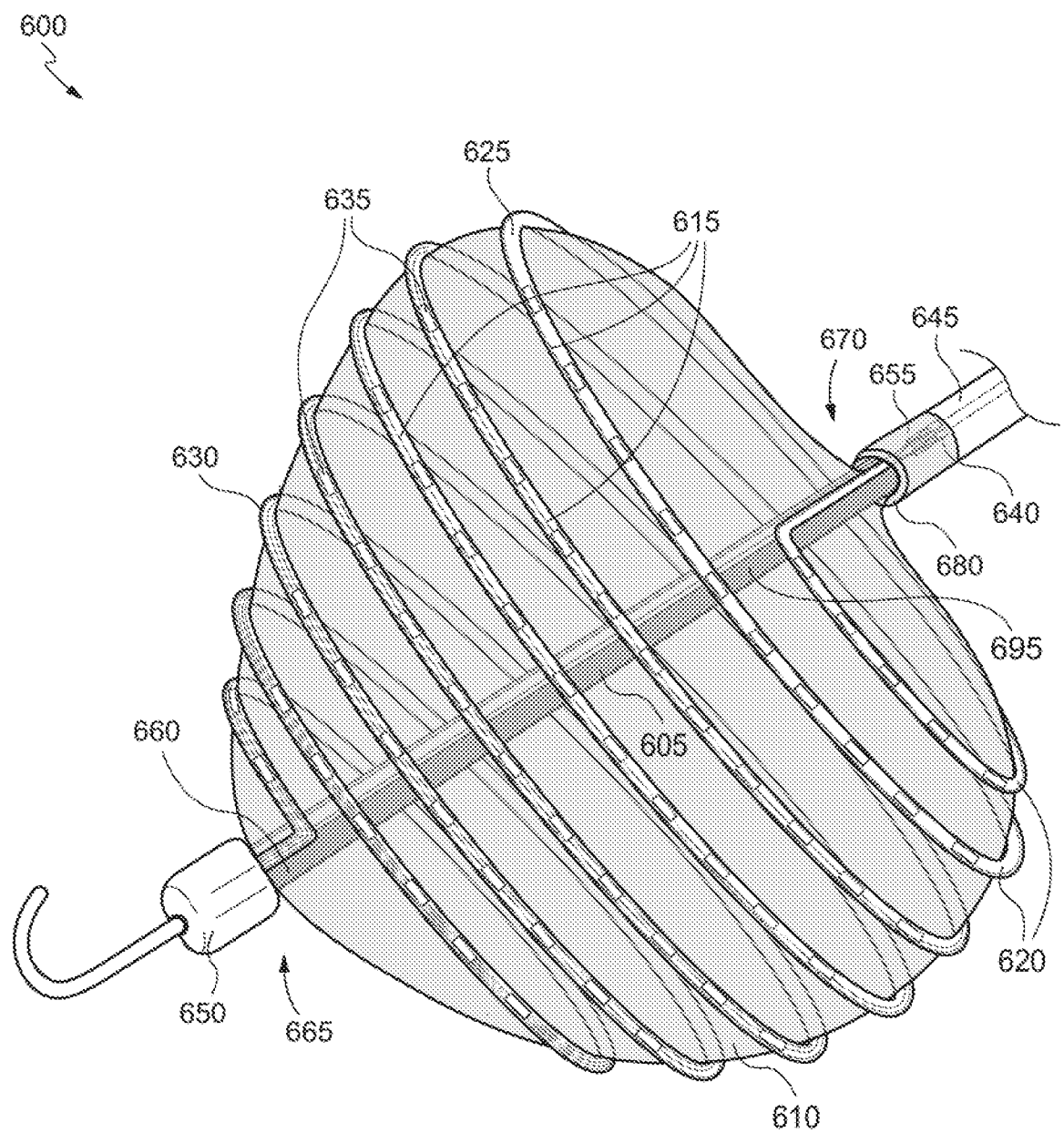
FIG. 6B shows a perspective view of an alternative medical device in an inflated configuration in accordance with various embodiments.

FIGS. 6A and 6B show a medical device 600 (e.g., an alternative version of the medical device 500 as discussed with respect to FIGS. 5A-5I) in accordance with some aspects of the present invention. In various embodiments, the medical device 600 includes a hollow core 605, a balloon 610 disposed over at least a portion of the hollow core 605, and a flexible framework 615 comprising one or more thin film elements 620 (e.g., splines or thin film elements as discussed with respect to FIGS. 1A, 1B 1C, 2A, 2B, 2C, 3A, and 3B) formed on at least a portion of the balloon 610. The one or more thin film elements 620 comprise one or more layers of dielectric material 625, one or more conductive traces 630, one or more electrodes 635 electrically connected to the one or more conductive traces 630 and one or more contacts 640 electrically connected to the one or more conductive traces 630. The medical device 600 may further include a cable 645 comprising a plurality of wires electrically connected to the one or more contacts 640. In certain embodiments, the medical device 600 further includes an end cap 650, a sheath 655 and a travel limiter 660 disposed between the one or more thin film elements 620 and the hollow core 655. The hollow core 605 extends between the end cap 650 and the sheath 655.

The one or more thin film elements 620 may extend from a proximal end 650 of the balloon 610 to a distal end 655 of the balloon 610. In some embodiments, a length of the one or more thin film elements 620 equals approximately half of a perimeter of the balloon 610 in an inflated state. In certain embodiments, the length of the one more thin film elements 620 is between 20 mm and 100 mm, for example about 36 mm. The one or more electrodes 635 may be distributed on the one or more thin film elements 620 in an arbitrary or in a predetermined pattern. For example, each of the one or more thin film elements 620 may comprise two or more electrodes 635 disposed in a northern hemisphere region of the balloon 610 (between the mid-point of the balloon 610 and the distal end 665). Alternatively, each of the one or more thin film elements 620 may comprise two or more electrodes 635 disposed in a southern hemisphere region of the balloon 610 (between the mid-point of the balloon 610 and the proximal end 670). Alternatively, each of the one or more thin film elements 620 may comprise two or more electrodes 635 disposed across the northern hemisphere region and the southern hemisphere region of the balloon 610. Alternatively, each of the one or more thin film elements 620 may comprise two or more electrodes 635 disposed in a central region of the balloon 610 (near the mid-point of the balloon 610). In some embodiments, any number of the electrodes 635 are replaced with one or more sensors (e.g., pressure or temperature sensors).

As shown in FIG. 6A, the one or more thin film elements 620 may be a plurality of thin film elements 620, each thin film element of the plurality of thin film elements 620 may extend longitudinally from a distal end 680 of the sheath 655 to the end cap 650 and each thin film element of the plurality of thin film elements 620 is attached to the end cap 650. The plurality of thin film elements 620 are formed on an outer surface of the balloon 610 and maintain the same contour as the outer surface of the balloon 610. As shown in FIG. 6B, the one or more thin film elements 620 may be a single thin film element 620, the single thin film element extends from a distal end 680 of the sheath 655 to the end cap 650 in a helix around the balloon 610, and the single thin film element may be attached to the end cap 650. The single thin film element may be formed on an outer surface of the balloon 610 and maintain the same contour as the outer surface of the balloon 610.

V. Methods of Deploying Integrated Catheter Devices and Systems

Figure 7:
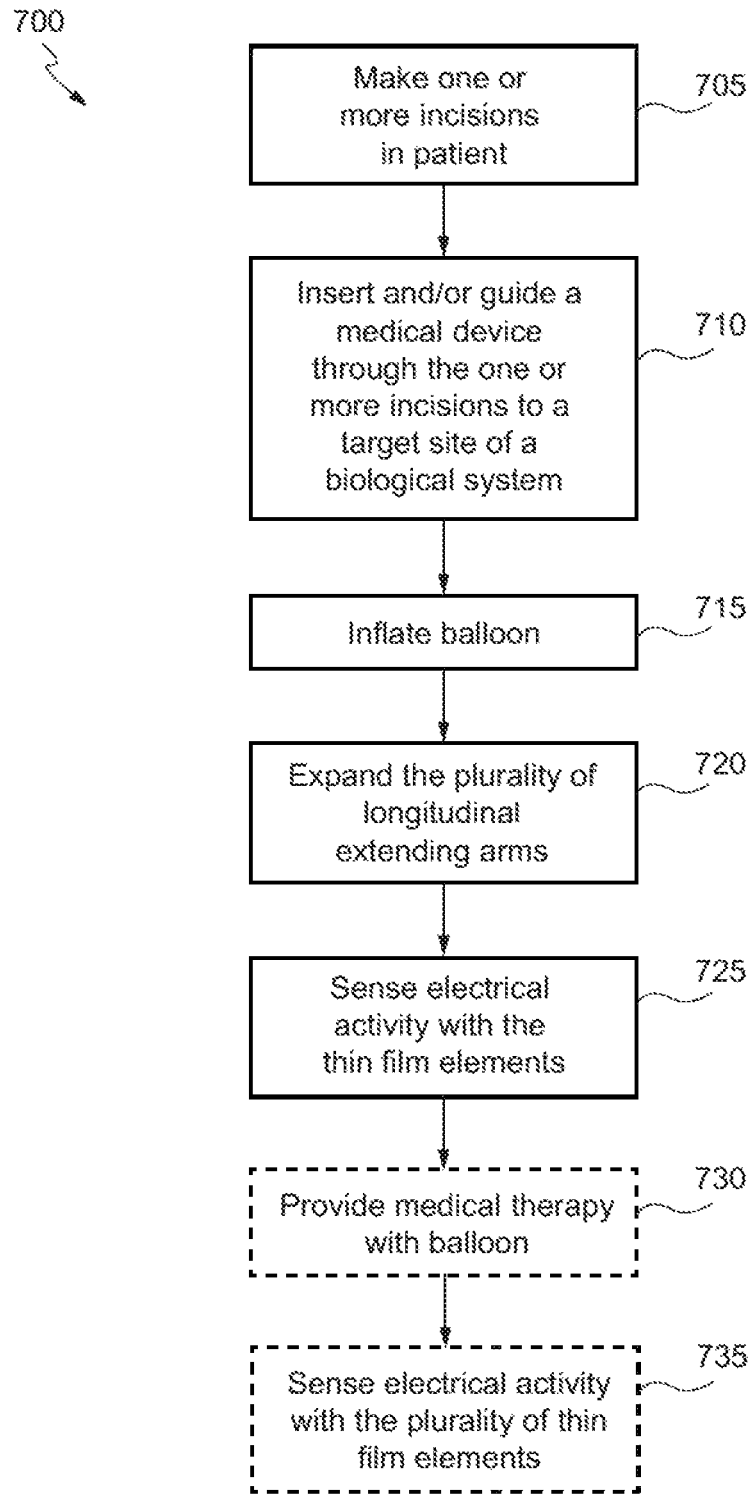
FIG. 7 shows a flow diagram of an alternative process for using a medical device or system in accordance with various embodiments.

FIG. 7 depicts a simplified flowchart depicting processing performed for accessing a site of a target biological structure in a patient and delivering a medical device or system for mapping and optionally providing medical therapy to the site of the target biological structure according to various embodiments. As noted herein, the flowchart of FIG. 7 illustrates the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented manually by a user such as a surgeon or by special purpose hardware-based systems that perform the specified functions or acts, or combinations of special purpose hardware and computer instructions.

FIG. 7 depicts a simplified flowchart 700 illustrating a process used by user to access, map, and optionally provide treatment to a site of a target biological structure in a patient. In some embodiments, the site of the target biological stricture is accessed using the medical devices or systems described with respect to FIGS. 5A-5I, 6A, and 6B. At step 705, one or more incisions are made in a patient to access a target biological structure. At step 710, the medical device or system is inserted and/or guided into a cavity of a body through the one or more incisions to a target site of the biological system. In some embodiments, the medical device includes a sheath; a balloon disposed over at least a portion of the sheath; and a flexible framework comprising one or more thin film elements formed on at least a portion of the balloon. The one or more thin film elements comprise a plurality of mapping electrodes.

At step 715, the balloon is inflated. At step 720, the one or more thin film elements are expanded prior to or with the inflation of the balloon. In some embodiments, each of the one or more thin film elements moves in a radial direction from the central axis (A). In some embodiments, each of the one or more thin film elements take on a contoured shape of the inflated balloon. At step 725, the one or more thin film elements are used to sense electrical activity at a site within the cavity and map the activity on a three-dimensional model of the biological system. At optional step 730, a medical therapy (e.g., cryoablation) is provided by the balloon to the site within the cavity of the body based at least on the activity mapped on the three-dimensional model of the biological system. At optional step 735, the one or more thin film elements are used to sense electrical activity at the site within the cavity to confirm whether the medical therapy was successful. As should be understood, one or more of steps 715, 720, 725, 730, and 735 can be performed sequentially or simultaneously.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A medical device comprising:
   a hollow core;
   a balloon disposed over at least a portion of the hollow core;
   a flexible framework comprising one or more thin film elements formed on at least a portion of the balloon, wherein the one or more thin film elements comprise a plurality of mapping electrodes;
   an end cap;
   a sheath, wherein the hollow core extends between the end cap and the sheath;
   a travel limiter disposed between the one or more thin film elements and the hollow core; and
   a pull cable disposed within the sheath and attached to the end cap or the hollow core for retracting the hollow core and anchoring the travel limiter to a distal end of the sheath.

2. The medical device of claim 1, wherein the one or more thin film elements further comprise a plurality of conductive tracings in electrical communication with the plurality of mapping electrodes.

3. The medical device of claim 1, further comprising a proximal hub positioned on or within the sheath, wherein:
   the sheath comprises a channel; and
   the one or more thin film elements extend through the channel of the sheath and connect with the proximal hub.

4. The medical device of claim 1, wherein:
   the one or more thin film elements are a plurality of thin film elements;
   each thin film element of the plurality of thin film elements extends longitudinally from a distal end of the sheath to the end cap; and
   each thin film element of the plurality of thin film elements is attached to the end cap.

5. The medical device of claim 1, wherein:
the one or more thin film elements are a single thin film element;
the single thin film element extends from a distal end of the sheath to the end cap in a helix around the balloon; and
the single thin film element is attached to the end cap.

6. The medical device of claim 5, wherein the balloon is a cryoballoon.

7. A medical device comprising:
a sheath;
an end cap;
a hollow core extending from the sheath to the end cap;
a plurality of thin film elements disposed around the hollow core, wherein the plurality of thin film elements comprise a plurality of mapping electrodes;
a travel limiter disposed between the plurality of thin film elements and the hollow core; and
a pull cable disposed within the sheath and attached to the end cap or hollow core for retracting the hollow core and anchoring the travel limiter to a distal end of the sheath.

8. The medical device of claim 7, wherein the plurality of thin film elements are made of one or more layers of dielectric material.

9. The medical device of claim 8, wherein the dielectric material is a polymer of imide monomers, a liquid crystal polymer (LCP), parylene, polyether ether ketone (PEEK), or any combination thereof.

10. The medical device of claim 9, wherein the plurality of mapping electrodes are comprised of one or more layers of conductive material, and the conductive material is platinum (Pt), platinum/iridium (Pt/Ir), titanium (Ti), gold/titanium (Au/Ti), any alloy thereof, or any combination thereof.

11. The medical device of claim 7, further comprising a guide wire disposed in the sheath and extending from an opening in the end cap.

12. The medical device of claim 7, wherein the plurality of thin film elements further comprise a plurality of conductive tracings in electrical communication with the plurality of mapping electrodes.

13. The medical device of claim 7, further comprising a proximal hub positioned on or within the sheath, wherein:
the sheath comprises a channel; and
the plurality of thin film elements extend through the channel of the sheath and connect with the proximal hub.

14. The medical device of claim 7, wherein:
each thin film element of the plurality of thin film elements extends from a distal end of the sheath to the end cap in a straight line parallel to a central axis of the hollow core; and
each thin film element of the plurality of thin film elements is attached to the end cap.

15. The medical device of claim 7, wherein:
each thin film element of the plurality of thin film elements extends from a distal end of the sheath to the end cap in a helix around the hollow core; and
each thin film element of the plurality of thin film elements is attached to the end cap.

16. A medical system comprising:
a mapping catheter comprising:
a sheath comprising a proximal end, a distal end, a channel, and a hub disposed at the proximal end;
an end cap;
a hollow core extending from the distal end of the sheath to the end cap;
a flexible framework comprising a plurality of longitudinal extending arms disposed around the hollow core, wherein the plurality of longitudinal extending arms comprise a plurality of mapping electrodes, distal ends of the plurality of longitudinal extending arms are attached to the end cap, the plurality of longitudinal extending arms extend through the channel of the sheath, and proximal ends of the plurality of longitudinal extending arms are attached to the hub; and
a travel limiter attached to the end cap and disposed between the plurality of longitudinal extending arms and the hollow core;
a pull cable disposed within the sheath and attached to the end cap or the hollow core for retracting the hollow core and anchoring the travel limiter to a distal end of the sheath; and
a treatment catheter disposed over at least a portion of the mapping catheter.

17. The medical system of claim 16, wherein the treatment catheter is a cryoballoon catheter comprising a cryoballoon disposed over a hollow body, and wherein the hollow body is disposed over the sheath of the mapping catheter.

* * * * *